(12) United States Patent
Tomasi et al.

(10) Patent No.: US 11,786,117 B2
(45) Date of Patent: *Oct. 17, 2023

(54) MOBILE DEVICE APPLICATION FOR OCULAR MISALIGNMENT MEASUREMENT

(71) Applicant: Massachusetts Eye and Ear Infirmary, Boston, MA (US)

(72) Inventors: Matteo Tomasi, Boston, MA (US); Shrinivas Pundlik, Boston, MA (US); Kevin Edward Houston, Norwell, MA (US); Gang Luo, Lexington, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 233 days.

This patent is subject to a terminal disclaimer.

(21) Appl. No.: 17/084,412

(22) Filed: Oct. 29, 2020

(65) Prior Publication Data

US 2021/0113079 A1 Apr. 22, 2021

Related U.S. Application Data

(63) Continuation of application No. 16/076,592, filed as application No. PCT/US2017/018213 on Feb. 16, 2017, now Pat. No. 10,849,492.

(Continued)

(51) Int. Cl.
*A61B 3/08* (2006.01)
*A61B 3/15* (2006.01)
(Continued)

(52) U.S. Cl.
CPC .............. *A61B 3/085* (2013.01); *A61B 3/00* (2013.01); *A61B 3/08* (2013.01); *A61B 3/10* (2013.01);
(Continued)

(58) Field of Classification Search
CPC .. A61B 3/085; A61B 3/08; A61B 3/00; A61B 3/10; A61B 3/14; A61B 3/152;
(Continued)

(56) References Cited

U.S. PATENT DOCUMENTS 9,734,586 B2 8/2017 Luo et al.
2007/0146631 A1 6/2007 Sinclair et al.
(Continued)

FOREIGN PATENT DOCUMENTS

CN 1695547 A 11/2005
CN 102961117 A 3/2013
(Continued)

OTHER PUBLICATIONS

Dimitrov et al.. Measuring Rod and Cone Dynamics in Age-Related Maculopathy, Investigative Ophthalmology & Visual Science, 2008,49(1):55-65.
(Continued)

*Primary Examiner* — Cara E Rakowski
(74) *Attorney, Agent, or Firm* — QUARLES & BRADY LLP

(57) ABSTRACT

Disclosed are a mobile device and method which include acquiring, by an image acquisition unit installed in a mobile device, an image of eyes of a patient while light provided by a light source reflects from an optical surface of the eyes of the patient; and obtaining, by a processor installed in the mobile device, ocular misalignment measurements, including a magnitude and a direction of ocular misalignment in the eyes of the patient, using the acquired image or set of images.

16 Claims, 13 Drawing Sheets

Related U.S. Application Data

(60) Provisional application No. 62/295,869, filed on Feb. 16, 2016.

(51) Int. Cl.

| | | |
|---|---|---|
| *A61B 3/00* | (2006.01) | |
| *A61B 3/10* | (2006.01) | |
| *A61B 3/14* | (2006.01) | |
| *G06V 10/141* | (2022.01) | |
| *G06V 10/10* | (2022.01) | |
| *G06V 10/147* | (2022.01) | |
| *G06V 40/19* | (2022.01) | |
| *G06V 40/18* | (2022.01) | |
| *G06V 40/60* | (2022.01) | |

(52) U.S. Cl.
CPC ............... *A61B 3/14* (2013.01); *A61B 3/152* (2013.01); *G06V 10/141* (2022.01); *G06V 10/147* (2022.01); *G06V 10/17* (2022.01); *G06V 40/19* (2022.01); *G06V 40/193* (2022.01); *G06V 40/67* (2022.01)

(58) Field of Classification Search
CPC ............ G06K 9/00604; G06K 9/0061; G06K 9/2027; G06K 9/209; G06K 9/22; G06K 9/00912
See application file for complete search history.

(56) References Cited

U.S. PATENT DOCUMENTS

| | | | |
|---|---|---|---|
| 2009/0079937 A1 | 3/2009 | Chen et al. | |
| 2009/0316111 A1 | 12/2009 | Hunter et al. | |
| 2011/0150334 A1 | 6/2011 | Du et al. | |
| 2011/0157550 A1* | 6/2011 | Chen ..................... | A61B 3/145 351/246 |
| 2011/0163955 A1 | 7/2011 | Nasiri et al. | |
| 2013/0235346 A1 | 9/2013 | Huang et al. | |
| 2014/0268051 A1 | 9/2014 | Maor et al. | |
| 2014/0285768 A1 | 9/2014 | Barnard et al. | |
| 2015/0085096 A1 | 3/2015 | Smits | |
| 2015/0265146 A1 | 9/2015 | Bloom et al. | |

FOREIGN PATENT DOCUMENTS

| | | |
|---|---|---|
| CN | 103476325 A | 12/2013 |
| GB | 2496005 A | 5/2013 |
| WO | 2011021936 A1 | 2/2011 |
| WO | 2014195951 A1 | 12/2014 |
| WO | 2015070023 A2 | 5/2015 |
| WO | 2016001796 A1 | 1/2016 |
| WO | 2017143091 A1 | 8/2017 |
| WO | 2019165262 A1 | 8/2019 |
| WO | 2019165263 A1 | 8/2019 |
| WO | 2019195450 A1 | 10/2019 |

OTHER PUBLICATIONS

Gaffney et al., The Effect of Pre-Adapting Light Intensity on Dark Adaptation in Early Age-Related Macular Degeneration, Documenta Ophthalmologica, 2013, 127(3):191-199.
Hogg et al., Visual Function and Dysfunction in Early and Late Age-Related Maculopathy, Progress in Retinal and Eye Research, 2006, 25:249-276.
Iannaccone, Measuring Dark Adaptation in the Elderly: A Predictor of Who May Develop Macular Degeneration?, Investigative Ophthalmology & Visual Science, 2014, 55(8):4790.
Jackson et al., Aging and Dark Adaptation, Vision Research, 1999, 39:3975-3982.
Jackson et al., A Short-Duration Dark Adaptation Protocol for Assessment of Age-Related Maculopathy, Journal of Ocular Biology Disease and Informatics, 2008, 1:7-11.
Jackson et al., Diagnostic Sensitivity and Specificty of Dark Adaptometry for Detection of Age-Related Macular Degeneration, Investigative Ophthalmology & Visual Science, 2014, 55(3):1427-1431.
Kretschmer et al., A System to Measure the Optokinetic and Optomotor Response in Mice, Journal of Neuroscience Methods, 2015, 256:91-105.
Kretschmer et al., OMR-Arena: Automated Measurement and Stimulation System to Determine Mouse Visual Thresholds Based on Optomotor Responses, PLOS ONE, 2013, 8(11):e78058, 12 pages.
Owsley et al., Psychophysical Evidence for Rod Vulnerability in Age-Related Macular Degeneration, Investigative Ophthalmology & Visual Science, 2000, 41(1):267-273.
Owsley et al., Delays in Rod-Mediated Dark Adaptation in Early Age-Related Maculopathy, Ophthalmology, 2001, 108(7):1196-1202.
Owsley et al., Cone- and Rod-Mediated Dark Adaptation Impairment in Age-Related Maculopathy, Ophthalmology, 2007, 114(9):1728-1735.
Owsley et al., Associations Between Abnormal Rod-Mediated Dark Adaptation and Health and Functioning in Older Adults with Normal Macular Health, Investigative Ophthalmology & Visual Science, 2014, 55(8):4776-4789.
Phenosys, Technology for Research in Animal Behaviour, Website: http://www.phenosys.com, Copyright 2011-2020 By PhenoSys GmbH, 8 pages.
Prusky et al., Rapid Quantification of Adult and Developing Mouse Spatial Vision Using a Virtual Optomotor System, Investigative Ophthalmology & Visual Science, 2004, 45(12):4611-4616.
PCT International Search Report and Written Opinion, PCT/US2017/018213, dated Apr. 25, 2017, 14 pages.
European Patent Office, Extended Search Report, Application No. 17753856.8, dated Oct. 11, 2019, 7 pages.
European Patent Office, Communication Pursuant to Article 94(3) EPC, Application No. 17753856.8, dated Dec. 15, 2022, 4 pages.

\* cited by examiner

MOBILE DEVICE APPLICATION FOR OCULAR MISALIGNMENT MEASUREMENT

CROSS-REFERENCE TO RELATED APPLICATION

This Application is a Continuation of U.S. patent application Ser. No. 16/076,592 filed on Aug. 8, 2018, which is a U.S National Phase Application, filed under 35 U.S.C. § 371, of International Application No. PCT/US17/18213, filed on Feb. 16, 2017, which claims the benefit of U.S. Provisional Application 62/295,869 filed on Feb. 16, 2016. The entire contents of these applications are incorporated herein by reference in their entirety.

FEDERALLY SPONSORED RESEARCH AND DEVELOPMENT

This invention was made with government support under R43 EY025902 awarded by the National Institutes of Health. The government has certain rights in the invention.

TECHNICAL FIELD

The present disclosure relates generally to ocular misalignment measurement, and more particularly, to a mobile device application for ocular misalignment measurement.

BACKGROUND

Ocular misalignment, or, more commonly, eye misalignment, refers to a visual disorder in which the eyes are misaligned and point in different directions. When the eyes are misaligned, one eye will typically fixate on an object of interest while the other eye turns in another direction, such as inward (i.e., esotropia), outward (i.e., exotropia), down (i.e., hypotropia), or up (i.e., hypertropia). Ocular misalignment, which affects about 3 to 8% of the United States population, can lead to double vision, spatial confusion, and diminished depth perception if left untreated. Misalignment of the eyes in children can lead to amblyopia, which could lead to permanently reduced vision in one of the eyes (affecting about 4% of the population). Misalignment in adults can result in double vision and difficulty in depth perception. People with neurological disease such as multiple sclerosis or injury such as stroke, trauma are at greater risk of developing strabismus, and children below eight years of age are at additional risk for underdevelopment of vision due to strabismic amblyopia.

Heterophoria is a condition in which misalignment exists but is compensated under normal viewing conditions, and so there is no strabismus, or it is intermittent. The condition is revealed using tests which occlude an eye (dissociation) and look for drifting of the eye out (exophoria), in (esophoria), up (hyperphoria), or down (hypophoria). Patients with heterophoria are typically characterized as having eyes which point in different directions while in a resting state (eyes closed or in a dark environment). With such patients, the tendency of the eyes to deviate is kept latent by binocular fusion during typical viewing conditions, and symptoms of double vision do not occur or are intermittent. People with heterophoria may experience eye strain and reduced visual endurance.

Strabismus is a condition that interferes with binocular vision by preventing a person from directing both eyes simultaneously towards a single fixation point. That is, the eyes are unable to gaze at once to the same point in space. Strabismus usually results in normal vision in the preferred sighting (or "fixating") eye—the eye that the patient prefers to use—but may cause abnormal vision in the deviating or strabismic eye. Due to the misalignment between the images being projected to the brain from the two eyes, the brain tends to suppress the images from the deviated eye. Such misalignment may be constant or intermittent, and symptoms of strabismus include double vision, visual confusion, incoordination, reduced vision in the deviated eye in childhood onset, and higher risk of falls in the elderly.

Unless detected and treated, e.g., through corrective lenses, eye patches, vision therapy, surgery, and the like, cases of ocular misalignment can result in permanent problems with visual development. Early ophthalmologic diagnosis and treatment can substantially reduce the risk of developing permanent vision loss, such as amblyopia (i.e., lazy eye), in the deviated eye. Effective treatment can allow for normalization of vision development, realignment of the eyes, and restoration of stereo or three-dimensional vision.

Ocular misalignment can be diagnosed and measured using several different techniques. The measurements help quantify a risk factor for the patient developing an ocular misalignment condition, such as amblyopia. One technique, known as light reflex testing, or Hirschberg testing, involves directing a patient to look at a point of light in front of the patient's face and observing where the light reflects off the corneas. When performing the test, the ocular reflections (i.e., light reflexes) on the corneal surface of both eyes caused by the light are compared. In a patient with normal fixation, the ocular reflections in both eyes will be substantially symmetrical. In a patient exhibiting ocular misalignment, the ocular reflections will be asymmetrical.

Notably, a photographic version of Hirschberg testing can be used to quantify the magnitude and direction of ocular misalignment in the patient. In this case, a photograph of the patient's eyes is acquired, and characteristics of the patient's eyes are analyzed using the acquired photograph. Conventional clinical practice for ocular misalignment measurement, however, can be tedious, subjective, and requires significant amount of subject cooperation and doctor's expertise. Meanwhile, automated devices using photographic analysis, while helpful, are expensive, and limited to specialty clinics. Thus, the accessibility to convenient and inexpensive machines is currently hindered.

SUMMARY OF THE DISCLOSURE

The present disclosure provides for a mobile device application and a mobile device which performs said mobile device application to automatically measure ocular misalignment in the eyes of a patient by acquiring an image or a set of images of the patient using the mobile device and providing quantifiable measures of misalignment based on the acquired image. The application uses conventional mobile device hardware, including a built-in camera and flash, to capture a photograph of the eyes of a patient while light from the flash is shined in the patient's eyes and reflects from a corneal surface thereof (alternatively, light may be provided by an external source). After a photograph of the patient's eyes is captured, the application automatically processes the photograph to measure the magnitude of ocular misalignment. The entire processing is performed locally on the mobile device itself; thus, the application is not required to send captured pictures to a remote server for processing. Based on the measurements, magnitude of strabismus is measured and a risk of the patient developing a condition, such as amblyopia, can be quantified and provided to the patient.

In particular, a camera of a mobile device can be directed toward the eyes of the patient. The application can provide guidance to the patient, examiner, or other user to adjust the distance between the mobile device and the patient's face and the angle of the mobile device camera with respect to the patient's eyes. As the eyes of the patient fixate on a particular object, the mobile device can capture a photograph of the patient's eyes while light from the built-in flash, or otherwise, reflects from an optical surface of the eyes (e.g. cornea). The application then performs a variety of calculations to measure the ocular misalignment, including detecting the iris, pupil, limbus boundary, and corneal reflection, and then converting the detected features into the real space (e.g., physical measurements, mm or prism diopters). Then, the magnitude of ocular misalignment can be calculated and displayed for the reference of the patient, doctor, or other user.

According to embodiments of the present disclosure, a method includes: acquiring, by an image acquisition unit installed in a mobile device, an image of eyes of a patient while light provided by a light source reflects from an optical surface of the eyes of the patient; and obtaining, by a processor installed in the mobile device, ocular misalignment measurements, including a magnitude and a direction of ocular misalignment in the eyes of the patient, using the acquired image.

The obtaining of ocular misalignment measurements may include: detecting a reflection on the corneal surface of a left eye of the patient and a reflection on the corneal surface of a right eye of the patient using the acquired image; and comparing a position of the reflection in the left eye to a position of the reflection in the right eye. The obtaining of ocular misalignment measurements may further include: detecting a reference point in the left eye and a reference point in the right eye using the acquired image; calculating a first distance between a position of the reference point in the left eye and the position of the ocular reflection in the left eye; calculating a second distance between a position of the reference point in the right eye and the position of the ocular reflection in the right eye; and calculating a difference between the first distance and the second distance.

Additionally, the obtaining of ocular misalignment measurements may further include measuring the positions of the reflections in the left and right eyes and the positions of the reference points in the left and right eyes in image space using the acquired image. The reference points in the left and right eyes may relate to a center of an iris or a pupil of the patient. The obtaining of ocular misalignment measurements may further include converting the first distance and the second distance into degrees or prism diopters using a Hirschberg ratio and an internal calibration factor based on iris diameter.

The method may further include diagnosing a condition of the patient based on the ocular misalignment measurements. The diagnosis may be performed according to the calculated difference between the first distance and the second distance. Further, the diagnosing of the condition may include: comparing the calculated difference between the first distance and the second distance to a predetermined misalignment threshold; and determining the condition of the patient based on the comparison of the calculated difference to the predetermined misalignment threshold. Also, the diagnosing of the condition may further include diagnosing the patient with a condition associated with ocular misalignment when the calculated difference is greater than or equal to the predetermined misalignment threshold.

The method may further include detecting an iridoscleral border and a pupillary margin of the eyes of the patient using the acquired image. The iridoscleral border and the pupillary margin may be detected using an adaptive thresholding algorithm.

In addition, the mobile device may be a smart phone or a tablet. The light source may be a flash producing device installed in the mobile device configured to produce a flash of light during the acquisition of the image. The light source can be independent of the mobile device. Further, the image acquisition unit may be a rear-facing camera installed in the mobile device. In the alternative, the image acquisition unit may be a front-facing camera installed in the mobile device. The method may further include recognizing an input provided by a user to initiate the acquisition of the image of the eyes of the patient using a rear-facing camera installed in the mobile device, where the user and the patient are not the same. Alternatively, the method may further include recognizing an input provided by a user to initiate the acquisition of the image of the eyes of the patient using a front-facing camera installed in the mobile device, where the user and the patient are the same.

The method may further include: acquiring a plurality of images of the eyes of the patient; determining an image quality of the acquired plurality of images; and using an image having a highest image quality among the acquired plurality of images for the measuring of the magnitude of ocular misalignment in the eyes of the patient. Also, the method may further include: acquiring a plurality of images of the eyes of the patient; obtaining the ocular misalignment measurements in each of the acquired images; generating a composite of the obtained ocular misalignment measurements; and determining an overall ocular measurement based on the generated composite.

During the acquisition of the image of eyes of the patient, both eyes of the patient may fixate on a point located on the mobile device. Alternatively, one eye of the patient may fixate on an external object while the other eye of the patient cannot view the external object due to a positioning of the mobile device.

The method may further include: acquiring a plurality of images of the eyes of the patient, where the eyes of the patient fixate on a different target for each of the plurality of acquired images; and obtaining ocular misalignment measurements in the eyes of the patient in each of the plurality of acquired images. In this regard, the method may further include calculating a Hirschberg ratio of the patient based on the ocular misalignment measurements. The method may further include: detecting an iris diameter and an inter-pupillary distance of the patient based on the acquired image; and calculating the Hirschberg ratio of the patient based further on the detected iris diameter and inter-pupillary distance of the patient. Also, the method may further include: assisting a user in positioning the mobile device to obtain a predefined angular change in position of the different targets relative to the eyes during the acquisition of the plurality of images.

Additionally, the method may further include: measuring a kappa angle between an optical axis and a visual axis of the eyes of the patient based on the acquired image; and diagnosing a condition of the patient based further on the measured kappa angle. In this regard, during the acquisition of the image of eyes of the patient, one eye of the patient may fixate on the light provided by the light source. The method may further include diagnosing which eye of the eyes of the patient is misaligned and a misalignment direction of the misaligned eye based on the kappa angle. Further, the method may include measuring a fixation reliability index of the non-misaligned eye based on a deviation of the non-misaligned eye from the kappa angle. Even further, the method may include calculating an accommodative convergence/accommodation (AC/A) ratio of the eyes of the patient based on the acquired image.

The method may further include compensating for a rotation of the mobile device when the mobile device is rotated during the acquisition of the image. Measurements obtained by one or more motion sensors installed in the mobile device may be used for the compensation of rotation of the mobile device.

Moreover, the method may further include detecting features in the eyes of the patient including a pupil, an iris, a limbus boundary, and a reflection on the optical surface using the acquired image. In this regard, the method may further include measuring positions of the detected features in the eyes of the patient in image space according to the acquired image. The method may further include detecting intermittent ocular misalignment motions in the eyes of the patient.

Additionally, the method may further include displaying information on a display screen of the mobile device for assisting in the acquisition of the image of eyes of the patient. The method may further include displaying a graphic on a display screen of the mobile device for assisting in aligning the eyes of the patient with the image acquisition unit. In this regard, the graphic may include a boundary surrounding both of the eyes of the patient or boundaries surrounding each of the eyes of the patient, respectively. Also, the method may further include displaying information relating to at least one of: a diagnosed ocular misalignment condition of the patient, a determined risk factor of the patient developing a condition associated with ocular misalignment, and the ocular misalignment measurements, on a display screen of the mobile device. The method may further include transmitting information relating to at least one of: a diagnosed ocular misalignment condition of the patient, a determined risk factor of the patient developing a condition associated with ocular misalignment, and the ocular misalignment measurements, to an external vision care provider.

Moreover, the method may include associating information relating to at least one of: a diagnosed ocular misalignment condition of the patient, a determined risk factor of the patient developing a condition associated with ocular misalignment, and the ocular misalignment measurements, with personal information of the patient.

The method may further include acquiring, by the image acquisition unit, a video of the eyes of the patient, where the acquired image is a frame selected among a plurality of frames of the acquired video. In this regard, the method may further include: acquiring, by the image acquisition unit, the video of the eyes of the patient while a cover sequence of the eyes of the patient is performed using an occluder; and generating, by the mobile device, one or more sounds to assist in the performance of the cover sequence.

Furthermore, in accordance with embodiments of the present disclosure, a mobile device includes: an image acquisition unit configured to acquire an image of eyes of a patient while light provided by a light source reflects from an optical surface of the eyes of the patient; and a processor configured to obtain ocular misalignment measurements, including a magnitude and a direction of ocular misalignment in the eyes of the patient, using the acquired image.

The mobile device may further include a flash producing device installed in the mobile device configured to produce a flash of light during the acquisition of the image, where the light source is the flash producing device.

Furthermore, in accordance with embodiments of the present disclosure, a non-transitory computer readable medium containing program instructions for performing a method includes: program instructions that obtain ocular misalignment measurements, including a magnitude and a direction of ocular misalignment in eyes of a patient, using an image acquired by an image acquisition unit while light provided by a light source reflects from an optical surface of the eyes of the patient.

BRIEF DESCRIPTION OF THE DRAWINGS

The embodiments herein may be better understood by referring to the following description in conjunction with the accompanying drawings in which like reference numerals indicate identically or functionally similar elements, of which.

Figure 1:
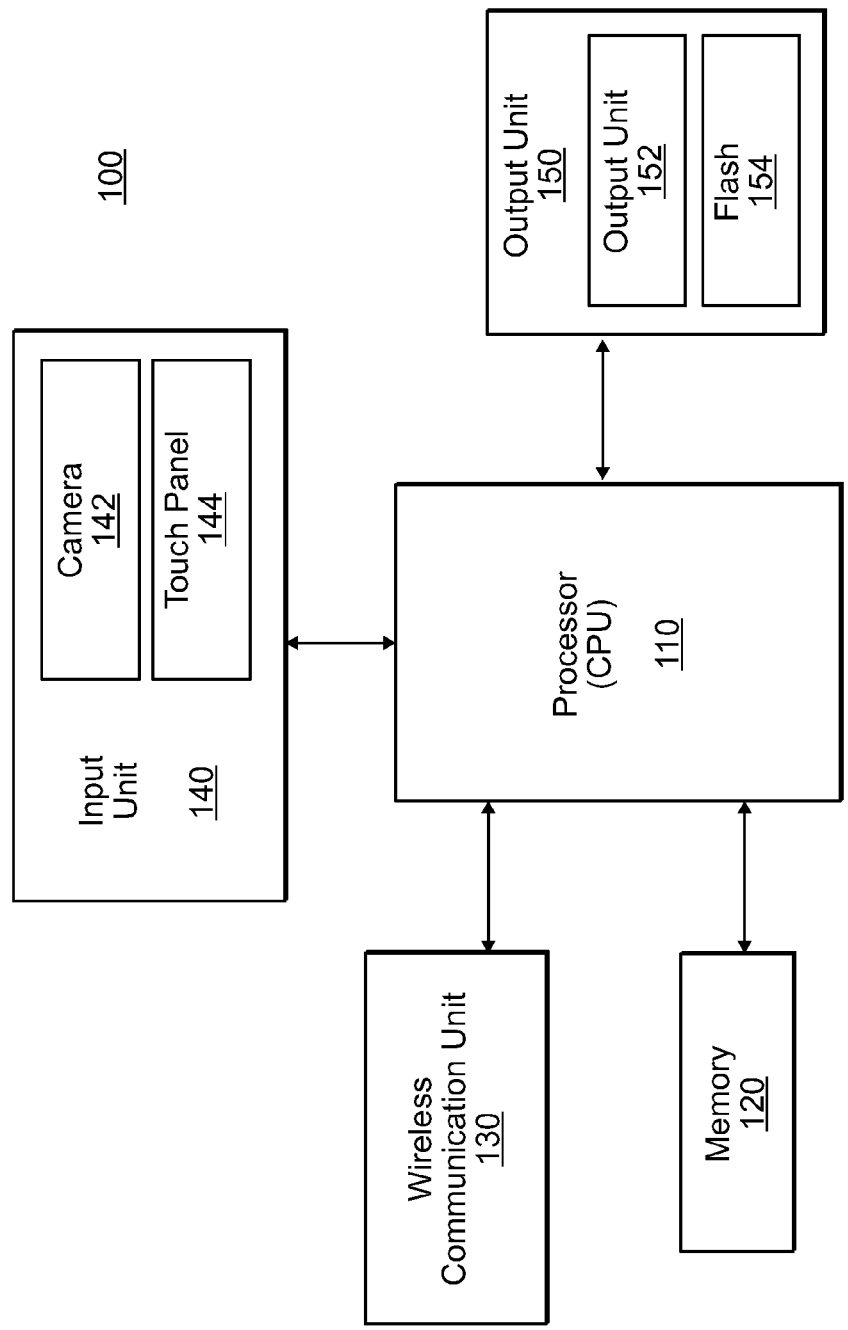
FIG. 1 is a diagrammatic view illustrating an exemplary mobile device architecture.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION OF THE EMBODIMENTS

Hereinafter, embodiments of the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled" denotes a physical relationship between two components whereby the components are either directly connected to one another or indirectly connected via one or more intermediary components.

It is understood that the term "mobile device" or other similar term as used herein is inclusive of any portable computing device, such as smart phones, tablets, laptops, PDAs, and the like. A "mobile device," as used herein, is not necessarily limited to devices which are conveniently portable, but may also include personal computers (PCs) or other similar computing machines. As referred to herein, a "mobile device" is equipped with, at least, one or more processors, as is generally known in the art, and an image acquisition unit (e.g., camera) allowing for a user to capture a photograph of a given subject. Further, a "mobile device" is preferably equipped with communication components, either wired or wireless, allowing for the device to communicate with external devices via a communication network. Similarly, the terms "mobile device application," "mobile application," or "application," as used herein, refer to a computer program executable by a processor installed in a "mobile device," as is generally known in the art.

It is also understood that the term "patient" or other similar term as used herein is inclusive of any subject on whom an ocular misalignment assessment could be performed. The term "user" as used herein is inclusive of any entity capable of interacting with or controlling a mobile device. The "user" may also be the "patient," or the "user" and "patient" may be separate entities, as described herein.

Additionally, it is understood that one or more of the below methods, or aspects thereof, may be executed by at least one processor. The processor may be implemented in a mobile device, as described herein. A memory configured to store program instructions may also be implemented in the mobile device, in which case the processor is specifically programmed to execute the stored program instructions to perform one or more processes which are described further below. Moreover, it is understood that the below methods may be executed by a mobile device comprising the processor, in conjunction with one or more additional components, as described in detail below.

Furthermore, the methods, or aspects thereof, of the present disclosure may be embodied as non-transitory computer readable media on a computer readable medium containing executable program instructions executed by the processor. Examples of the computer readable mediums include, but are not limited to, ROM. RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Referring now to embodiments of the present disclosure, conditions associated with ocular misalignment, including amblyopia, strabismus, and heterophoria, among others, affect 3 to 5% of the United States population, with studies showing that only one-third of pre-school children in the United States receive any form of vision screening. The combined cost of amblyopia screening (using current technology) and strabismus surgery in the United States is estimated to be $800 million annually, while the cost to society from loss of function is estimated at well over $20 billion. It is apparent, therefore, that accessibility to convenient and inexpensive screening devices should be improved.

To this end, techniques are disclosed herein relating to a mobile device application for ocular misalignment measurement. Without using external accessories or attachments, the mobile application can measure ocular misalignment, including, but not limited to, tropias (i.e., eye deviation during binocular fixation) and phorias based on a snapshot or a series of snapshots of a patient's eyes captured by a camera equipped in the mobile device. After a photograph of the patient's eyes is captured, the application can automatically process the photograph to measure the magnitude of ocular misalignment. By taking advantage of high-resolution cameras installed in many modern mobile devices, in conjunction with the custom designed image processing algorithms described herein, a high accuracy of measurement can be achieved. The entire processing is performed locally on the mobile device itself; thus, the application is not required to send captured pictures to a remote server for processing. (Though, it is also possible to implement a cloud-based screening device whereby the captured pictures are sent from the mobile device to a remote server for processing.) Based on the obtained measurements, a condition (such as strabismus) can be diagnosed, and a risk factor for the patient developing a condition (such as amblyopia) can be quantified and provided to the patient on the mobile device.

FIG. 1 illustrates an example diagrammatic view of a mobile device architecture according to embodiments of the present disclosure. As shown in FIG. 1, a mobile device 100 may contain multiple components, including, but not limited to, a processor (e.g., central processing unit (CPU) 110, a memory 120, a wireless communication unit 130, an input unit 140, and an output unit 150. It should be noted that the architecture depicted in FIG. 1 is simplified and provided merely for demonstration purposes. In view of the wide variety of commercially available mobile devices, the architecture of the mobile device 100, which is referenced throughout the present disclosure, can be modified in any suitable manner as would be understood by a person having ordinary skill in the art, in accordance with the present claims. Moreover, the components of the mobile device 100, themselves, may be modified in any suitable manner as would be understood by a person having ordinary skill in the art, in accordance with the present claims. Therefore, the mobile device architecture depicted in FIG. 1 should be treated as exemplary only and should not be treated as limiting the scope of the present disclosure.

Components of the mobile device 100 will be briefly described hereinbelow; though a detailed description thereof is well known in the art and thus will be omitted from the present disclosure. The processor 110 is capable of controlling operation of the mobile device 100. More specifically, the processor 110 may be operable to control and interact with multiple components installed in the mobile device 100, as shown in FIG. 1. For instance, the memory 120 can store program instructions that are executable by the processor 110. The mobile application described herein may be stored in the form of program instructions in the memory 120 for execution by the processor 110. The wireless communication unit 130 can allow the mobile device 100 to transmit data to and receive data from one or more external devices via a communication network. The input unit 140 can enable the mobile device 100 to receive input of various types, such as audio/visual input, user input, and the like. To this end, the input unit 140 may be composed of multiple input devices for accepting input of various types, including, for instance, a camera 142 (i.e., an "image acquisition unit"), touch panel 144, microphone (not shown), one or more buttons or switches (not shown), one or more motion sensors (not shown), and so forth. The input devices included in the input 140 may be manipulated by a user. For instance, a user can capture a photograph using the camera 142 by pressing the touch panel 144 in a recognized manner (i.e., a manner recognized by the processor 110). The camera 142 may include a front-facing camera and/or a rear-facing camera. Notably, the term "image acquisition unit," as used herein, may refer to the camera 142, but is not limited thereto. For instance, the "image acquisition unit" may refer to a program that acquires an image of a patient stored locally in the memory 120 or remotely on a server. The output unit 150 can display information on the display screen 152 for a user to view. The output unit 150 may further include a flash producing device 154 (i.e., "flash") which is a light source capable of producing a beam of light. The flash producing device 154 can be configured to produce a flash of light during acquisition of an image by the camera 142.

Figure 2:
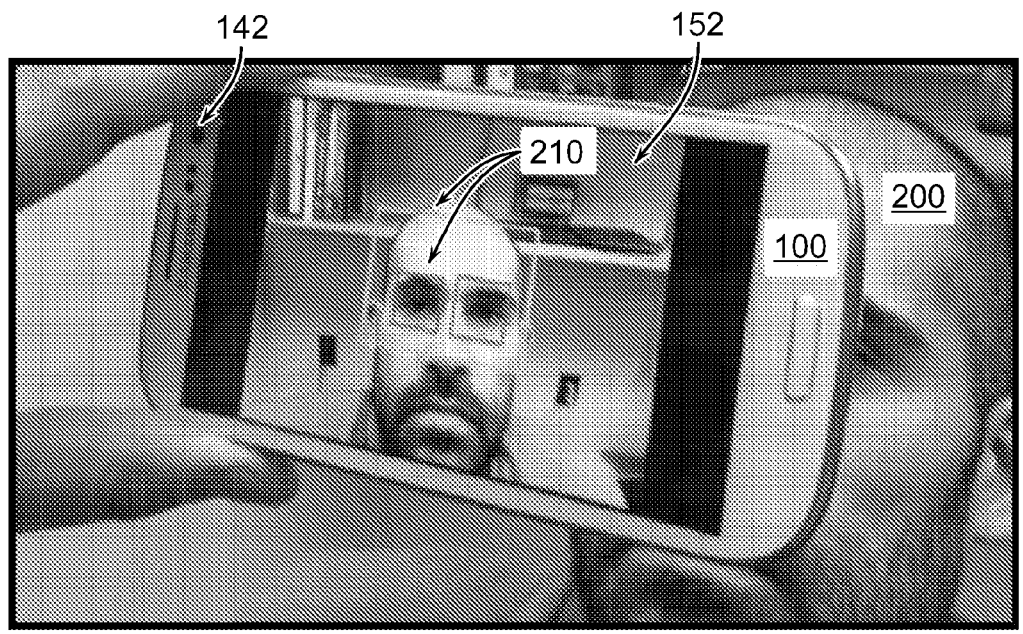
FIG. 2 is a view showing an example of the mobile device acquiring an image of eyes of a patient.

As explained above, the mobile device 100 can be programmed in a manner allowing it to perform the techniques for ocular misalignment screening described hereinbelow. In this regard, FIG. 2 illustrates an example view of the mobile device acquiring an image of eyes of a patient. As shown in FIG. 2, the mobile device 100 can be positioned in front of the face of a patient 200 and aligned with the eyes of the patient 200 so as to acquire an image of the eyes of the patient 200 using an image acquisition unit (e.g., rear- or front-facing camera 142) installed in the mobile device 100.

While the user attempts to position the mobile device 100 to capture a photograph of eyes of the patient 200, the mobile device 100 can provide guidance in real-time for the user in the form of instructions and/or graphics 210 displayed on the display screen 152 to assist the user in properly aligning the camera 142 with the patient 200, after which a photo can be taken. For instance, the displayed feedback can guide the user to align the mobile device 100 approximately 10 to 60 cm from the face of the patient 200, or more preferably approximately 20 to 50 cm from the face of the patient 200, or even more preferably approximately 30 to 40 cm from the face of the patient 200, such that both eyes are positioned within graphics 210 that are overlaid on the display screen 152. The graphics 210 may include, for instance, a first boundary that surrounds both eyes of the patient 200 to indicate an area of interest and second boundaries that surround each detected eye of the patient 200, respectively, as shown in FIG. 2. The displayed boundary or boundaries may be of a pre-defined shape, size, and/or position, or the shape, size, and/or position thereof may dynamically change based on information about the patient's eyes being detected by the camera 142 and processed by the processor 110 in real-time.

The patient 200 can then be instructed by the user of the mobile device 100 or by instructions displayed on the display screen 152 to fixate one or both eyes on a point (e.g., the camera 142, a point on the mobile device 100 itself, an external object, etc.), thus allowing for proper processing of the patient's eyes by the processor 110. In the case of strabismus testing, for example, measurement is performed binocularly, meaning that the patient 200 fixates on a specified target with both eyes, such as the camera 142.

The mobile device 100 can perform a photographic version of the Hirschberg test for ocular misalignment measurements. To this end, a light provided by a light source reflects from a corneal surface of the eyes of the patient 200 during acquisition of the image of the eyes of the patient 200 by the camera 142. When light is shined in the eyes of the patient 200, its reflection can be seen on the cornea. Thus, the photographic Hirschberg test, as implemented by the processor 110 of the mobile device 100, can measure the decentration, i.e., the horizontal and/or vertical displacement, of the corneal reflection from the center of the eye based on the acquired image of the patient's eyes, as described in further detail with respect to FIG. 3. The light source may be, for instance, the flash producing device 154 installed in the mobile device 100. As is known in the art, the flash producing device 154 can produce a flash of light during acquisition of an image by the camera 142. Alternatively, the light source may be any external light source (i.e., a light source independent of the mobile device 100, such as a lamp, flashlight, etc.) capable of providing a light that reflects from a corneal surface of the eyes of the patient 200.

As the user attempts to align the mobile device 100 with the eyes of the patient 200, such that a photograph sufficient for analysis by the processor 110 can be taken using the camera 142, the processor 110 can compensate for a rotation of the mobile device 100 when the mobile device 100 is rotated. The compensation may be achieved in two ways. First, the processor 110 can determine the amount of tilt of the mobile device 100 with respect to the eyes of the patient 200 and the amount of necessary tilt compensation, e.g., using motion sensor(s) installed in the mobile device 100, and real-time guidance can then be provided to the user by displaying instructions and/or graphics on the display screen 152 indicating to the user that the mobile device 100 should be tilted by an indicated amount. Second, the processor 110 can determine the amount of tilt of the mobile device 100 with respect to the eyes of the patient 200 and the amount of necessary tilt compensation after an image of the patient 200 has been taken. In this case, the processor 110 can perform image calculations to identify and compensate for the tilt present in the acquired image.

Once the user has aligned the mobile device 100 with the eyes of the patient 200, a photograph of the patient's eyes can be captured using an image acquisition unit installed in the mobile device 100. As described above, the term "image acquisition unit," as used herein, may refer to the camera 142, but is not limited thereto. For instance, the "image acquisition unit" may refer to a program that acquires an image of a patient stored locally in the memory 120 or remotely on a server. In the case that the image acquisition unit is the camera 142 installed in the mobile device 100, as shown in FIG. 2, the camera may be front-facing or rear-facing with respect to the mobile device 100. When using a rear-facing camera, the patient 200 may require that a separate user perform the image acquisition process (e.g., by holding the mobile device 100, aligning the mobile device with the patient's eyes, and pressing the designated shutter button as recognized by the processor 110), which is specifically shown in FIG. 2. When using a front-facing camera, however, the patient 200 may perform the image acquisition process by himself or herself, as the patient 200 is capable of viewing the display screen 152 to properly align the camera 142 with the patient's eyes prior to capturing the photograph.

Figure 3:
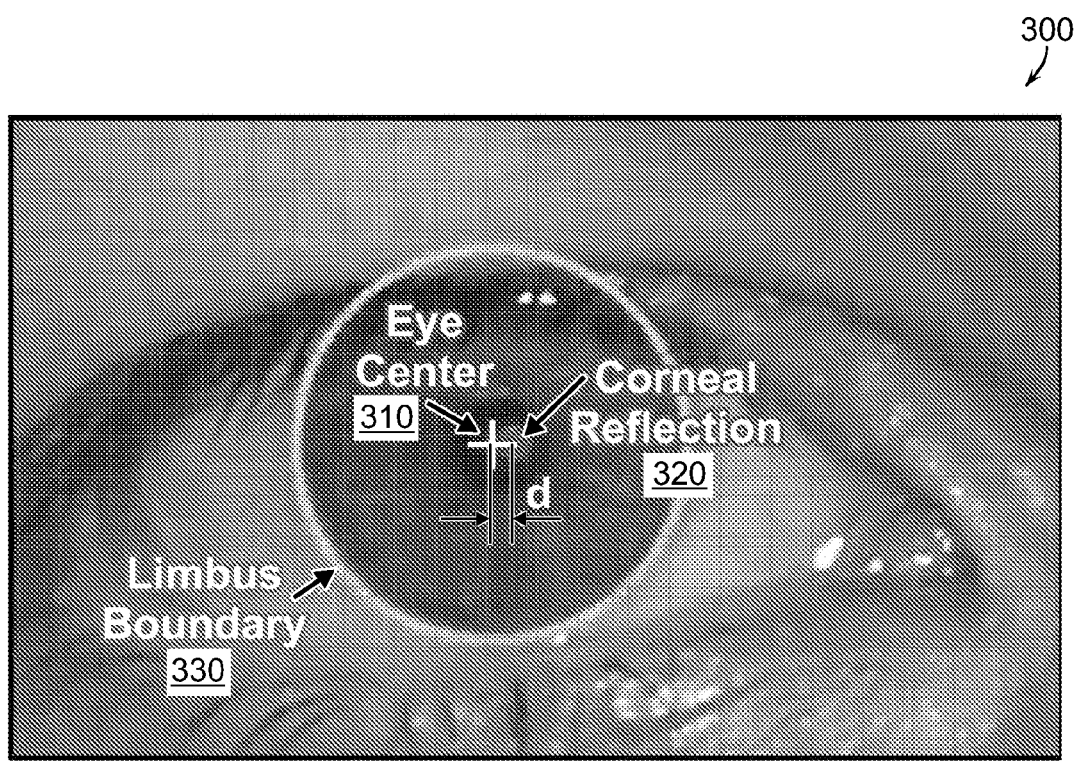
FIG. 3 is a view showing an exemplary image of an eye of a patient acquired by the image acquisition unit.

The magnitude of ocular misalignment in the eyes of the patient 200 can be measured using a variety of techniques, each of which requiring detecting one or more structures or features of the eyes of the patient 200. In this regard, FIG. 3 illustrates an example image of an eye of a patient acquired by the image acquisition unit. As shown in FIG. 3, the image 300 includes multiple features that can be detected by the processor 110 during processing of the image 300, including the eye center 310, the corneal reflection 320, the limbus boundary 330, the iridoscleral border, the pupillary margin, and the like, for the purpose of measuring ocular misalignment, including the amount and direction of misalignment.

Detecting such structures or features in the acquired image 300 may be achieved using a variety of suitable image processing algorithms, such as an adaptive thresholding algorithm, for example. According to one technique for measuring ocular misalignment, which is particularly useful for detecting the presence of strabismus in the patient 200, the processor 110 can detect in the acquired image 300 of the patient 200 an ocular reflection 320 on the corneal surface of both eyes and compare the position of the ocular reflection 320 in each eye to one another. More specifically, the processor 110 can compute a distance d between a reference point 310 (e.g., the eye center/pupil or iris) in each of the left and right eyes and the corneal reflection 320 caused by the light. The eye center can be calculated by computing a curve fitted to the limbus boundary 330. The position of the reference point 310 would be the same in each eye, but the position of the corneal reflection 320 in each eye may vary based on the amount of misalignment present in the eyes of the patient 200. Notably, the processor 110 can detect features in the eyes of the patient 200 regardless of the patient's eye color. Along these lines, the processor 110 can use the pupil region as a reference point for eyes with light color, rather than using the iris as a reference point.

When the eyes are aligned with each other, the distance d between the reference point 310 of the eye and the corneal reflection 320 is approximately the same in both the eyes, or less than a predetermined misalignment threshold. The misalignment threshold may be set by the clinician or user (e.g., one prism diopter (PD), two PD, three PD, etc.) based on a desired sensitivity and/or may be calibrated according to accuracy of the system being operated by processor 110. For instance, a presence of excessive noise in the system creates the risk for inaccurate measurements, and the misalignment threshold can be increased accordingly.

Conversely, a difference in the distance d between the two eyes is indicative of misalignment (any manifest eye deviation present under binocular fixation is termed as a tropia). To this point, a difference can be calculated between the distance d from the reference point 310 in the left eye to the corneal reflection 320 in the left eye (i.e., "first distance") and the distance d from the reference point 310 in the right eye to the corneal reflection 320 in the right eye (i.e., "second distance"). The calculated difference may then be compared to a predetermined misalignment threshold to ascertain whether the difference between the first distance and the second distance (i.e., the misalignment of the left and right eyes) is significant enough to diagnose a condition of the patient (e.g., strabismus, heterophoria, etc.). If the calculated difference is greater than or equal to the predetermined misalignment threshold, the processor 110 may determine that the patient 200 is suffering from a condition associated with ocular misalignment. The predetermined misalignment threshold may be stored in the memory 120 and retrieved from the memory 120 by the processor 110. The misalignment threshold may be predefined to a default value, such as three prism diopters, for example, and may be tuned according to the preference of the user.

In order to calculate the distance d between the reference point 310 and the ocular reflection 320 in a given eye, the position of the reference point 310 and the position of the ocular reflection 320 can be measured in image space using the acquired image 300 of the eyes of the patient 200. To this end, the positions of the reference point 310 (e.g., iris, pupil, limbus boundary, or the like) and the ocular reflection 320 is expressed in image space coordinates (e.g., pixels). In this manner, the distance d between the reference point 310 and the ocular reflection 320 in a given eye can be readily calculated.

Furthermore, the calculated distance d between the reference point 310 and the ocular reflection 320 can be converted into an objective measure such as prism diopters or degrees using a Hirschberg ratio (HR) computed for the patient 200 based on the image 300 and an internal calibration factor based on iris diameter. The Hirschberg ratio describes the relationship between the corneal reflection 320 decentration and the deviation of the eye. That is, the Hirschberg ratio determines how much angular deviation an eye would undergo for each millimeter of decentration of the corneal reflection 320. This ratio can be determined using population averages and can vary by about 4.5 prism diopters (standard deviation) from the mean value for a given patient. This variation ultimately affects the deviation measurement.

However, an accurate Hirschberg ratio for an individual can be determined if the patient 200 binocularly fixates on targets placed at known eccentricities with respect to the camera 142 (i.e., non-primary gaze directions, where the head is not facing forward). A plurality of images corresponding to each fixation, respectively, can be captured by the camera 142, and the eye deviations (both eyes separately) can be obtained in each image 300 using the techniques described above. Guidance can be provided to the user, e.g., by instructions and/or graphics displayed on the display screen 152, to assist the user in positioning the mobile device 100 to obtain a predefined angular change in position of the different targets (either on the mobile device 100 itself or a point that is not on the mobile device 100) relative to the eyes during the acquisition of the plurality of images. That is, the user can be assisted to obtain a predefined angular extent. The relationship between actual and measured eye deviations may then be used to determine the individualized Hirschberg ratio. That is, the Hirschberg ratio for the patient 200 call be calculated based on the measured magnitudes of ocular misalignment in the acquired images 300. Notably, the individualized Hirschberg ratio depends on the iris, pupil position, and angle Kappa of the patient 200. These, too, can be measured by the processor 110 when processing the acquired image 300.

In addition to performing Hirschberg ratio calculations, a plurality of images 300 of the patient 200 can be acquired in order to enhance the quality of the image to be processed by the processor 110. In one example, after acquiring a plurality of images 300 of the patient 200, the processor 110 can examine the images 300 to select one of the images having the highest quality. Then, the processor 110 can process the highest quality image 300 for the measuring of the magnitude of ocular misalignment. In another example, after acquiring a plurality of images 300 of the patient 200, ocular misalignment measurements can be obtained in each of the acquired images 300, and a composite of the obtained ocular misalignment measurements is generated. Then, an overall ocular measurement can be determined based on the generated composite. Additionally, measurements of deviation could be performed in each captured image, and an average or median of the measurements can be taken.

While tropias are manifest eye deviations, heterophorias (or phorias) are latent deviations which are not observed under binocular viewing conditions. As explained above, heterophorias occur when the fusion of the two eyes is broken with only one eye fixating. The non-fixating or deviating eye deviates from its initial position when not being used and returns to its normal position when the fusion is established again.

Thus, in order to measure heterophoria, another technique for measuring ocular misalignment can be performed, in which the patient 200 fixates on a target that is visible only to one eye as the mobile device 100, or other vision occluding object, blocks the other eye from viewing the target. This way, the fusion between the two eyes is broken, and the processor 110 can measure the deviation between the viewing eye and blocked eye.

Figure 4A:
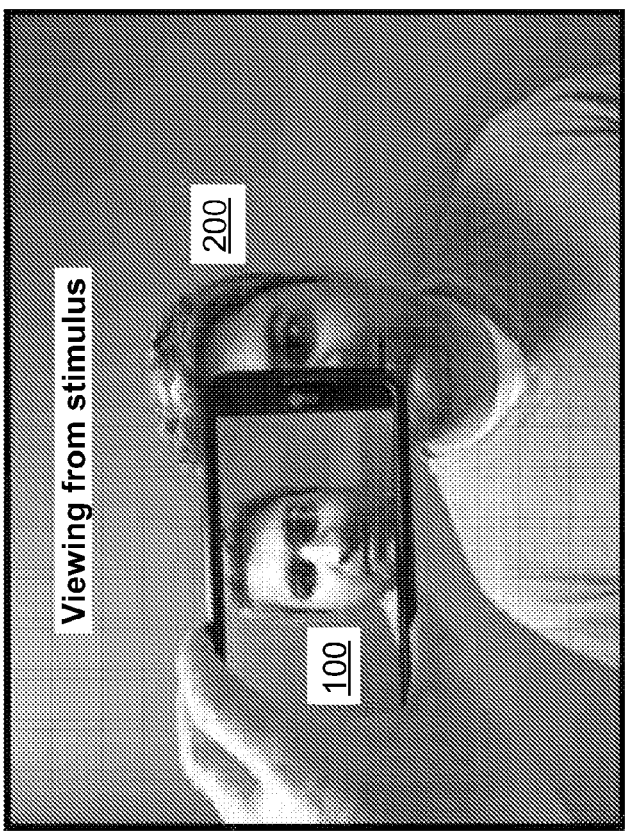
FIGS. 4A and 4B are views illustrating an example of the mobile device being used to perform heterophoria measurements.
Figure 4B:
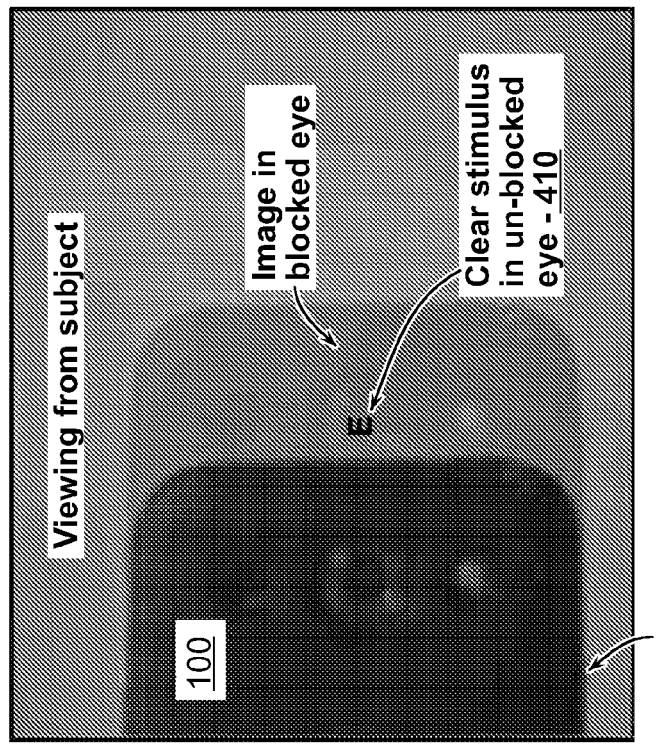

In this regard, FIGS. 4A and 4B illustrate example views of the mobile device being used to perform heterophoria measurements. As shown in FIG. 4A, a user may hold the mobile device 100 to acquire an image of the eyes of the patient 200, as previously demonstrated in FIG. 2. Here, however, the patient 200 fixates on an external target (or stimulus) 410 while the mobile device 100 is positioned such that only one of the patient's eyes is able to view the stimulus 410. As shown in FIG. 4B, the perspective of the patient (or subject) 200 shows that one eye has a clear, unblocked view of the external stimulus 410, while the other eye is precluded from viewing the stimulus by the positioning of the mobile device, allowing the blocked eye to deviate. Furthermore, when performing heterophoria measurements, the image acquisition unit may capture a plurality of images of the patient 200 fixating at near and far distances (using only one eye). The captured images can then be analyzed by the processor 110 to compute the amount of deviation between the eyes.

Notably, the results of a heterophoria measurement can be compared to the results of a strabismus measurement to diagnose and/or quantify either strabismus or heterophoria. When no misalignment is detected in the strabismus test, but misalignment is detected in the heterophoria test, a heterophoria can be diagnosed. On the other hand, when misalignment is detected in the strabismus test, the diagnosis is strabismus and not heterophoria, regardless of the results of the heterophoria test.

In addition, the Kappa angle can be calculated by the processor 110 based on the acquired image 300 of the patient 200 to assist in measuring the magnitude of ocular misalignment. The Kappa angle is the angle between the optical and the visual axis of the eye. Because the fovea is not completely aligned with the optical axis of the eye, there may be some offset that varies between individuals; the Kappa angle quantifies this offset.

The Kappa angle can be computed by the processor 110 when a single eye (monocular) of the patient 200 fixates on a light source (e.g., flash producing device 154), with the other eye covered. In this position, the camera 142 can acquire an image 300 of the patient 200, such that the processor 110 detects and processes the corneal light reflection decentration in one eye at a time, rather than performing differential measurements. Then, once the iris diameter and Hirschberg ratio are calculated, using the techniques described above, the Kappa angle can be calculated in terms of degrees by the processor 110. The calculated Kappa angle can further assist in diagnosing a condition of the patient 200. Also, the processor 110 can diagnose which eye of the patient 200 is misaligned and a misalignment direction of the misaligned eye based on the Kappa angle. Along these lines, the processor 110 can measure a fixation reliability index of the non-misaligned eye based on a deviation of the non-misaligned eye from the Kappa angle.

In one example, the Kappa angle can be used to measure whether misalignment is occurring in the right or left eye, as well as the direction of misalignment (e.g., eso or exo). Here, the processor 110 can select the eye with the Kappa angle closer to the predetermined population norm as the fixating eye (i.e., non-misaligned eye). The processor 110 can then measure the fixation reliability index, as mentioned above, based on the deviation of the fixating eye from the population norm Kappa angle. These measurements can be displayed on the display screen 152 for the patient's reference in the form of a score, a graphic, or other similar technique.

In another example, the processor 110 can measure the horizontal iris diameter of the patient 200 and use the diameter as the reference point. The processing algorithm can then be calibrated using a predetermined population norm of the reference point, for example, a horizontal iris diameter (HID) of 11.7 mm, or a physical measurement of the iris diameter performed by the patient 200 entered into the mobile device 100. The calibrated measurements can be used to convert biometric measurements (e.g., interpupillary distance, pupil diameter, Kappa angle, etc.) made in pixel space to physical space. As a result, the processor 110 can determine the consistency of testing distance from the patient's eye to the mobile device 100 on successive measurements using changes in the horizontal iris diameter or other biometric landmark between tests.

Moreover, the processor 110 may calculate an accommodative convergence/accommodation (AC/A) ratio (or convergence accommodation/convergence (CA/C) ratio) of the eyes of the patient 200 based on the acquired image 300 and the measured magnitude of ocular misalignment. A measurement of heterophoria in the eyes of the patient 200 can also assist in the calculation of the AC/A ratio. The AC/A ratio is a measure of how the two eyes work together, that is, how well the eyes can fixate on a single target. To attain the AC/A ratio, the ocular misalignment of the patient 200 may be measured in multiple iterations under different conditions, where the patient 200 attempts fixates with both eyes on the same object. For example, a first photograph of the patient 200 can be taken at a distance of one meter or greater away from the camera 142, where there is essentially no convergence/accommodation demand, and a second photograph of the patient 200 can be taken at a shorter distance, such as 40 centimeters. Using these multiple sets of measurements, the processor 110 can compute the AC/A ratio of the patient 200.

Figure 5:
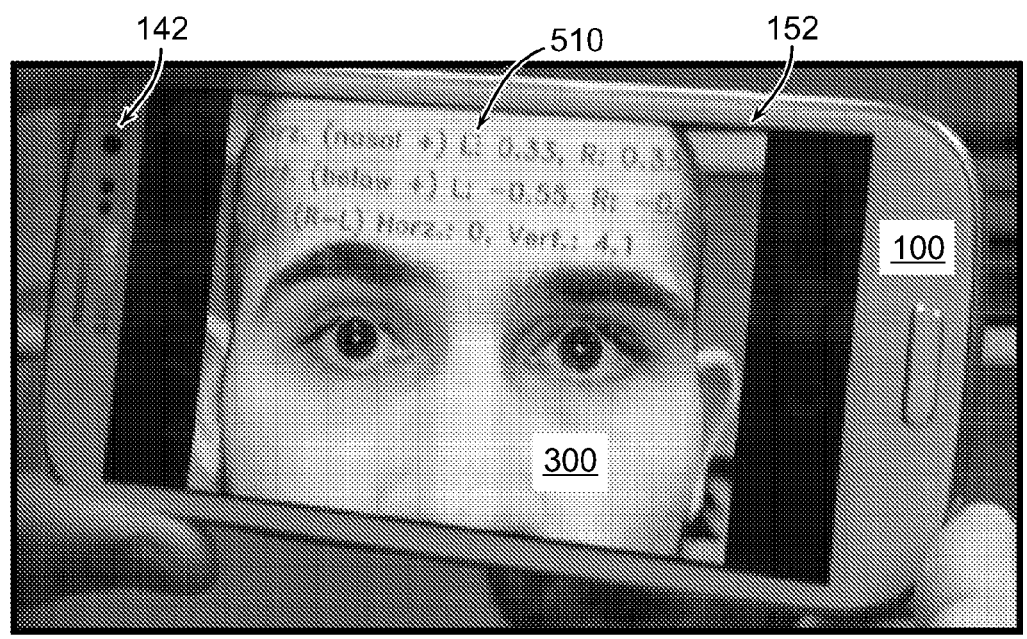
FIG. 5 is a view of an example of the mobile device showing feedback provided to the user after processing of the acquired image.

After the acquired image 300 of the patient 200 has been processed by the processor 110 to measure a magnitude of ocular misalignment, as explained in detail above, feedback can be provided to inform the patient 200 of the measurements taken. In this regard, FIG. 5 illustrates example feedback provided to the user (or patient) after processing of the acquired image. As shown in FIG. 5, after capture of the image 300 and subsequent processing of the image 300, feedback 510 indicating results of the measurements performed by the processor 110 can be displayed on the display screen 152 for the user's (or patient's) reference. The feedback 510 may include any information relevant to the computations performed by the processor 110 in processing the acquired image 300 of the patient 200 including, for example, a position of the pupil, a position of the iris, a position of the corneal reflection, eye deviation values, Hirschberg ratio, Kappa angle, AC/A ratio, and the like.

Further, the patient 200 may be informed of information indicating a diagnosed condition, such as strabismus, heterophoria, etc., of the patient 200 and/or a risk factor of the patient 200 developing a condition associated with ocular misalignment, such as amblyopia. The diagnosis and risk can be determined by the processor 110 based on the obtained ocular misalignment measurements, e.g., the amount of misalignment in each eye, the magnitude and/or direction of misalignment, etc.

The techniques disclosed herein can be applied for detecting related ocular conditions, such as nystagmus. Nystagmus is characterized by intermittent eye misalignment motions in the horizontal or vertical axis. The camera 142 can acquire a serial image or video along with a continuous or flashing light produced by the flash 154. Notably, nystagmus movements above a certain frequency of occurrence within a given time frame and eccentricities have been positively correlated with blood alcohol levels and are one of the roadside tests commonly used by police officers. Thus, the processor 110 may measure and interpret the frequency of events of misalignment occurring above a certain threshold magnitude and within a defined time/space span.

The mobile device 100 is capable of transmitting information relating to the ocular misalignment measurements, a diagnosis of the patient 200, and/or the determined risk of the patient 200 developing a condition associated with ocular misalignment to an external vision care provider (e.g., using the wireless transmission unit 130). The information can be transmitted automatically or in response to user input. Also, the information can be sent to the care provider via any suitable communication medium, including, but not limited to, wireless transmission, wired transmission, physical transfer (e.g., USB drive, paper records, etc.), and the like. This way, an external vision care provider can become aware of patients who may be in need of treatment and can develop treatment plans for such patients more efficiently.

Figure 7:
FIGS. 6-8 are screen-views illustrating an exemplary mobile application user interface.
Figure 6:
Figure 8:

FIGS. 6-8 illustrate example screen-views of a mobile application user interface. It is understood that the user interfaces depicted in FIGS. 6-8 do not limit the scope of the present claims and are merely presented for demonstration purposes. Thus, the user interface of the mobile application described herein may be modified in any suitable manner, as would be understood by a person of ordinary skill in the art.

As shown in FIG. 6, a registration page 600 can be presented to the patient 200. Here, the patient 200 can enter preliminary personal information. The processor 110 can associate the personal information of the patient 200 with the ocular misalignment measurements, the diagnosed condition of the patient 200, and/or the determined risk factor of the patient 200 developing a condition associated with ocular misalignment. The associated personal information may also be transmitted to the external vision care provider. The personal information may be stored locally in the memory 120 or remotely on a server. Alternatively, the personal information may be discarded. Storage of the above information may be controlled by the patient 200. For confidentiality purposes, the application may prompt the patient 200 for consent to store, send, or otherwise use the personal information of the patient 200.

As shown in FIG. 7, a profile page 700 can be presented to the patient 200 or to another user, such as a friend or family member of the patient 200, a medical professional, and so forth. Here, the profile page 700 can provide the patient's personal information, as well as a previously acquired photo(s) of the patient 200, if available. Additionally, if a misalignment assessment for the patient 200 was previously performed, the profile page 700 can provide information indicating the ocular misalignment measurements, the diagnosed condition, and/or the determined risk factor of the patient 200 developing an ocular misalignment condition. The information may be retrieved from the memory 120 or from a remote server.

As shown in FIG. 8, an image acquisition page 800 can be presented to the patient 200 allowing a user, or the patient himself or herself, to capture a photograph of the eyes of the patient 200. As explained with respect to FIG. 2, one or more boundaries 210 may be displayed on the image acquisition page 800 to assist the user in aligning the mobile device 100 with the patient's eyes. Additional controllable on-screen objects may be displayed on the image acquisition page 800, including, for instance, brightness control, flash activation, front- or rear-facing camera activation, zoom control, shutter button, and the like. After an image 300 of the patient 200 has been captured by the camera 142 (or otherwise acquired), and the acquired image 300 of the patient 200 has been processed by the processor 110 to measure a magnitude of ocular misalignment, feedback 510 can be provided to inform the patient 200 of the measurements taken, as demonstrated in FIG. 5.

Figure 9A:
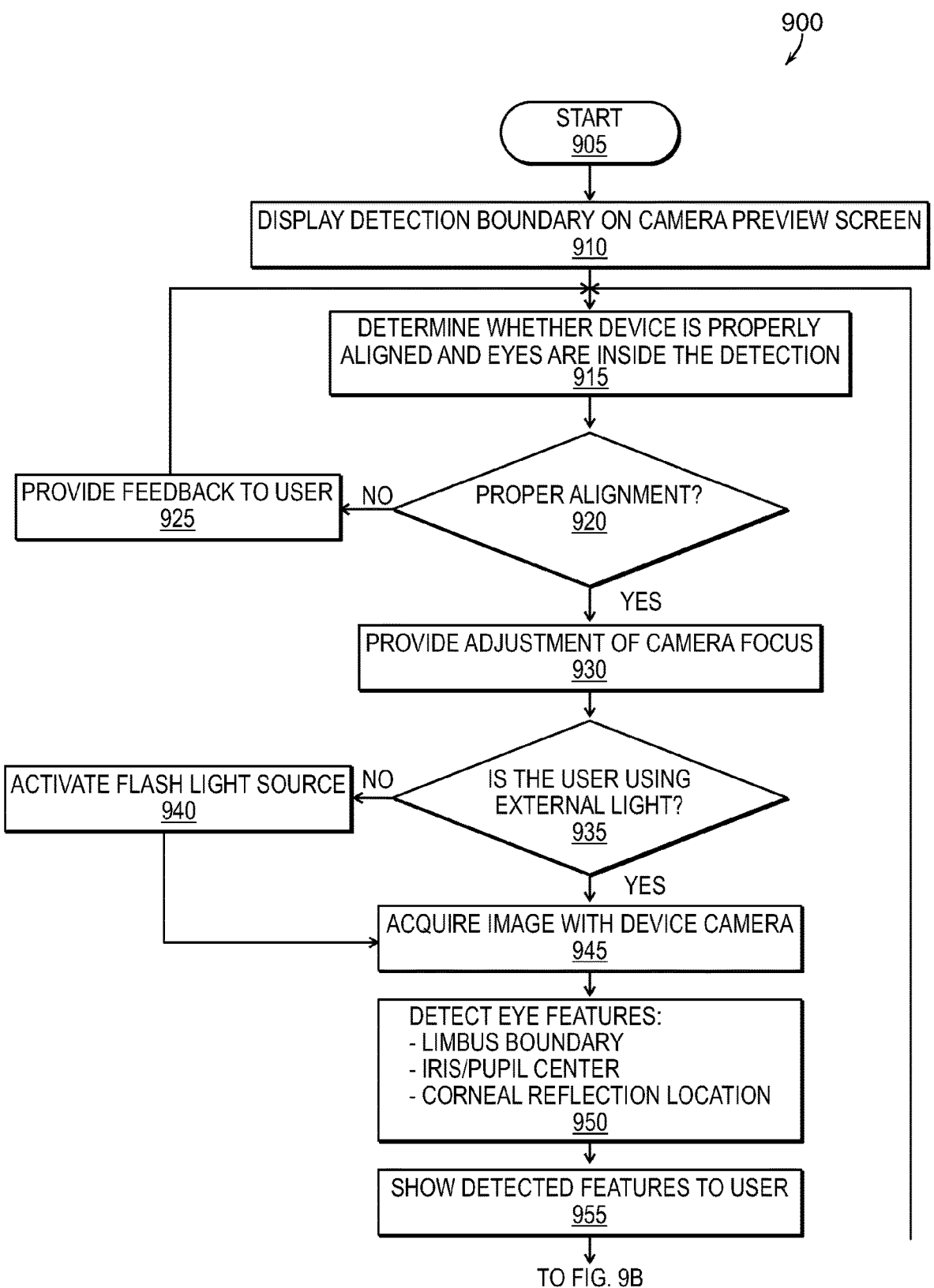
FIGS. 9A and 9B are flowcharts showing an exemplary simplified procedure for performing ocular misalignment measurement using the mobile device application described herein.
Figure 9B:
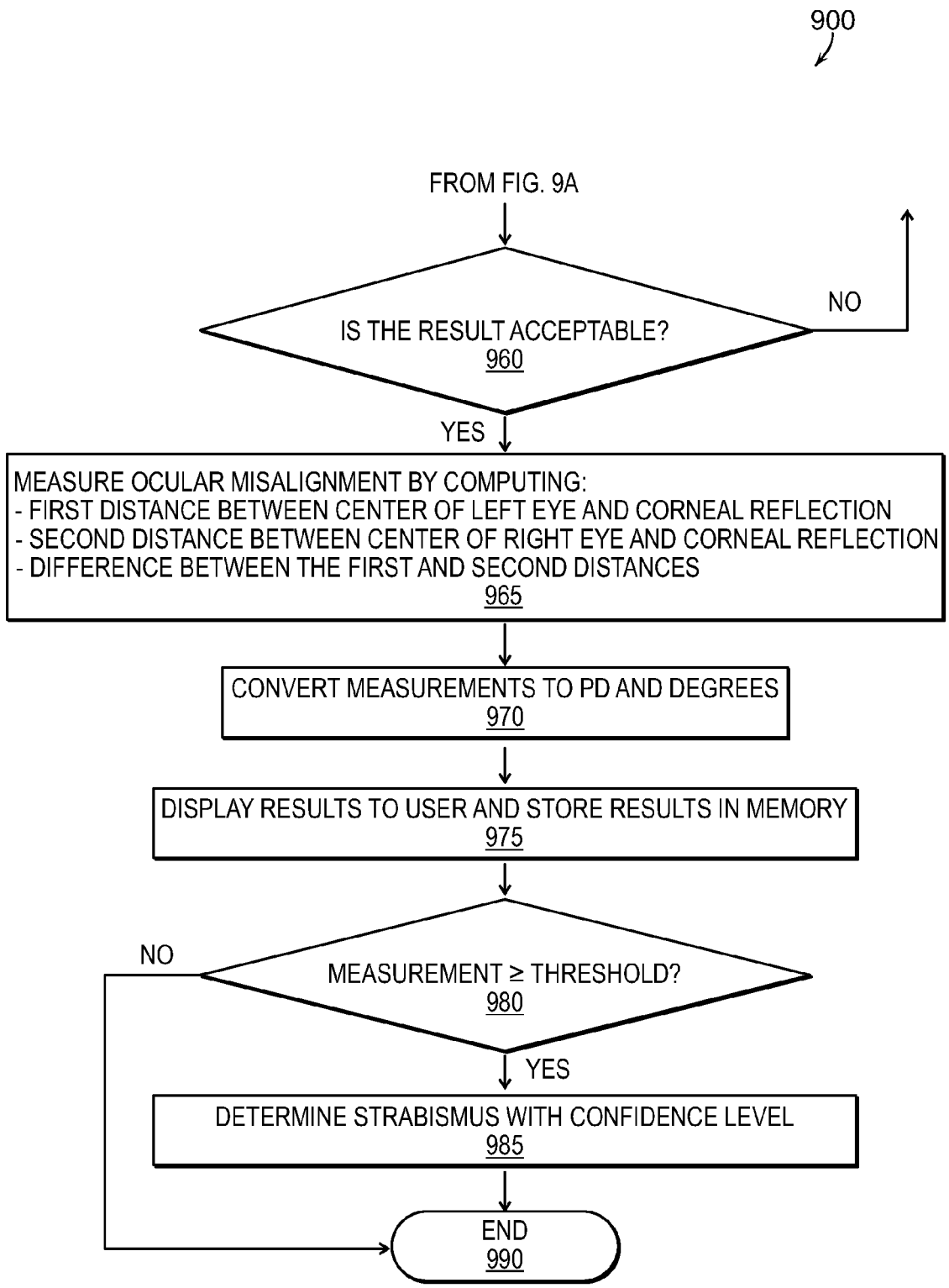

FIGS. 9A and 9B illustrate an example simplified procedure for performing ocular misalignment measurement using the mobile device application described herein. The procedure 900 may start at step 905, and continue to step 910, where, as described in greater detail herein, an image of the eyes of a patient 200 can be acquired and processed by the processor 110 to determine a magnitude of ocular misalignment in the patient's eyes.

At step 910, detection boundaries 210 can be displayed on a camera preview screen, such as the image acquisition page 800 shown in FIG. 8. The camera preview screen can be presented to the user on the display screen 152 of the mobile device 100 and can include a preview image of the subjects currently in view through the lens of the camera 142.

At step 915, the processor 110 can determine whether the mobile device 100 is properly aligned with the eyes of the patient 200. As the user attempts to align the mobile device 100 with the eyes of the patient 200, such that a photograph sufficient for analysis by the processor 110 can be taken using the camera 142, the processor 110 can automatically compensate for a rotation of the mobile device 100 when the mobile device 100 is rotated, such that the camera plane is parallel to the face of the patient 200. The compensation may be achieved in two ways. First, the processor 110 can determine the amount of tilt of the mobile device 100 with respect to the eyes of the patient 200 and the amount of necessary tilt compensation, and real-time guidance can be provided to the user by displaying instructions and/or graphics on the display screen 152 indicating to the user that the mobile device 100 should be tilted by an indicated amount (step 925). Second, the processor 110 can determine the amount of tilt of the mobile device 100 with respect to the eyes of the patient 200 and the amount of necessary tilt compensation after an image of the patient 200 has been taken. In this case, the processor 110 can perform calculations to identify and compensate for the tilt present in the acquired image.

Once the user has properly aligned the mobile device 100 with the patient 200, the focus of the camera 142 can be adjusted—either automatically or manually by the user (e.g., using on-screen controls)—so the patient's eyes are in clear view (step 930).

At step 935, the processor 110 can determine whether light is reflecting from a corneal surface of the eyes of the patient 200. The user can inform the processor 110 that an external light is being used, or the processor 110 can automatically detect if sufficient light is reflecting from the corneal surface of the patient's eyes.

If it is determined that an external light source is not being used, at step 940, the flash producing device 154 can be activated. As is known in the art, the flash producing device 154 can produce a flash of light during acquisition of an image by the camera 142. Thus, a photographic Hirschberg test, as implemented by the processor 110 of the mobile device 100, can measure the decentration, i.e., the horizontal and/or vertical displacement, of the corneal reflection from the center of the eye based on the acquired image of the patient's eyes, as described in further detail below.

At step 945, the camera 142 can capture an image 300 of the patient 200. As described above, the term "image acquisition unit," as used herein, may refer to the camera 142, but is not limited thereto. For instance, the "image acquisition unit" may refer to a program that acquires an image of a patient stored locally in the memory 120 or remotely on a server. In the case that the image acquisition unit is the camera 142 installed in the mobile device 100, the camera may be front-facing or rear-facing with respect to the mobile device 100. When using a rear-facing camera, the patient 200 may require that a separate user perform the image acquisition process, which is specifically shown in FIG. 2. When using a front-facing camera, however, the patient 200 may perform the image acquisition process by himself or herself, as the patient 200 is capable of viewing the display screen 152 to properly align the camera 142 with the patient's eyes prior to capturing the photograph.

At step 950, the acquired image 300 of the patient 200 can be processed by the processor 110 to detect a plurality of features in the eyes of the patient 200. The magnitude of ocular misalignment in the eyes of the patient 200 can be measured based on the detected features. As shown in FIG. 3, the acquired image 300 includes multiple features that can be detected by the processor 110 during processing of the image 300, including the eye center 310, the corneal reflection 320, the limbus boundary 330, the iridoscleral border, the pupillary margin, and the like, for the purpose of measuring ocular misalignment.

At step 955, the detected features can be displayed to the patient 200. The display screen 152 can provide the patient 200 with text-based information indicating the positions of the detected features listed above and/or the acquired image 300 of the patient 200 with graphics overlaid on the image 300 indicating the positions of the detected features.

At step 960, the patient 200 can confirm whether the results are acceptable. For instance, if the image 300 is blurry or tilted or the patient's eyes are not clearly visible, positions of the detected eye features may be erroneous. In such case, the patient 200 can opt to capture a new photograph, causing the procedure to return to step 915. Alternatively, the processor 110 can inform the patient 200 that the image 300 will not be sufficient for obtaining accurate measurements and prompt the user to capture a new photograph of the patient 200.

At step 965, the processor 110 measures the ocular misalignment based on the detected features of the patient's eyes in the acquired image 300. For instance, according to one technique for measuring ocular misalignment, which is particularly useful for detecting the presence of strabismus in the patient 200, the processor 110 can detect in the acquired image 300 of the patient 200 an ocular reflection 320 on the corneal surface of both eyes and compare the position of the ocular reflection 320 in each eye to one another. More specifically, the processor 110 can compute a distance d between a reference point 310 (e.g., the eye center) in each of the left and right eyes and the corneal reflection 320 caused by the light. The eye center can be calculated by computing a curve fitted to the limbus boundary 330. The position of the reference point 310 would be the same in each eye, but the position of the corneal reflection 320 in each eye may vary based on the amount of misalignment present in the eyes of the patient 200. Then, a difference can be calculated between the distance d from the reference point 310 in the left eye to the corneal reflection 320 in the left eye (i.e., "first distance") and the distance d from the reference point 310 in the right eye to the corneal reflection 320 in the right eye (i.e., "second distance").

At step 970, the calculated measurements can be converted into an objective measure such as prism diopters or degrees. The conversion can be performed using a Hirschberg ratio for the patient 200, which describes the relationship between the corneal reflection 320 decentration and the deviation of the eye, and an internal calibration factor based on iris diameter. Calculations for the Hirschberg ratio are described in detail above.

At step 975, the measurements of ocular misalignment can be presented to the patient 200. As shown in FIG. 5, feedback 510 indicating results of the measurements performed by the processor 110 can be displayed on the display screen 152 for the patient's reference. The feedback 510 may include any information relevant to the computations performed by the processor 110 in processing the acquired image 300 of the patient 200 including, for example, a position of the pupil, a position of the iris, a position of the corneal reflection, eye deviation values, Hirschberg ratio, Kappa angle, AC/A ratio, and the like. The measurements can also be stored in memory, either locally in memory 120 or remotely on a server.

At step 980, the processor 110 can determine whether the measurements are greater than or equal to a threshold value. In particular, the calculated difference between the "first distance" and the "second distance" may be compared to a predetermined misalignment threshold to ascertain whether the difference between the first distance and the second distance (i.e., the misalignment of the left and right eyes) is significant enough to determine that the patient is suffering from a condition associated with ocular misalignment (e.g., strabismus, heterophoria, etc.). If the calculated difference is greater than or equal to the predetermined misalignment threshold, the processor 110 may diagnose the patient 200 as having an ocular misalignment condition. The predetermined misalignment threshold may be stored in the memory 120 and retrieved from the memory 120 by the processor 110. The misalignment threshold may be predefined to a default value, such as three prism diopters, for example, and may be tuned according to the preference of the user.

At step 985, the processor 110 can determine whether the patient 200 has a condition associated with ocular misalignment, such as strabismus, based on the obtained ocular misalignment measurements. The processor 110 can determine a confidence level (i.e., a likelihood) of the patient 200 having strabismus, according to the measurements performed in steps 965 and 970. The display screen 152 can display these results to the patient 200. Additionally, the results can optionally be transmitted to an external vision care provider (e.g., using the wireless transmission unit 130).

The procedure 900 illustratively ends at step 990. The techniques by which the steps of procedure 900 may be performed, as well as ancillary procedures and parameters, are described in detail above.

It should be noted that the steps shown in FIG. 9 are merely examples for illustration, and certain other steps may be included or excluded as desired. Further, while a particular order of the steps is shown, this ordering is merely illustrative, and any suitable arrangement of the steps may be utilized without departing from the scope of the embodiments herein. Even further, the illustrated steps may be modified in any suitable manner in accordance with the scope of the present claims.

Example 1: Evaluation of Mobile Device Application for Measuring Eye Alignment

The mobile device application described herein performs an automated photographic Hirschberg test with goals of obtaining rapid, convenient, and quantifiable measurements of both manifest and latent eye deviations. To use the application, an examiner may ask the patient to fixate on a point (e.g., a rear-facing camera of the mobile device), and either capture a photo or record a video while covering or uncovering the patient's eyes. The mobile device application processes the captured image or video and computes the eye deviation based on de-centration of the corneal reflection.

In an effort to evaluate the mobile device application, eye deviations measured by the application were compared to the ground truth and within subjects in two separate trials for 25 normally sighted subjects fixating monocularly on targets covering an angular range of 46Δ (prism diopters (PD) can be shown using the symbol Δ). In another experiment, phoria measurements of 14 normally sighted subjects were compared between the application and the Modified Thorington (MT) method.

The results, as described below, demonstrate that a 95% confidence interval for repeated Hirschberg ratios (HR) obtained by the mobile device application was ±1.57Δ. Eye deviations measured by the application were correlated with the ground truth ($R^2=1.003$; $p<0.001$), with a root mean squared error (RMSE) of 1.7Δ for eye deviations within ±10Δ (2.4Δ over entire range). Phoria measurements with the application were strongly correlated with MT ($R^2=0.97$; $p<0.001$), with an error of $-0.76\pm1.6\Delta$. Accordingly, the mobile device application described herein can accurately and reliably measure a wide range of eye deviations and phoria that correlate closely with the conventional clinical method of MT.

A. Mobile Device Application

Using only a mobile device equipped with a camera, the mobile device application described herein can automatically detect ocular misalignment and provide an objective measure of eye deviation either from a single captured image or from a series of images of the patient's eyes. The patient may be asked to look at the mobile device camera, or any other suitable fixation target, depending on the test to be performed. Corneal reflection can be generated using either a built-in flash of the mobile device or external light source, such as lamp or eye chart light box. Processing of acquired images can be performed entirely within the mobile device's operating system, without the need for an internet connection or a remote server.

Strabismus measurements are typically performed with the patient fixating with both eyes on a specified target (e.g., a rear-facing camera of the mobile device). Image processing algorithms described herein can detect relevant features within each eye, including the limbus boundary, eye center, and corneal reflection, as shown in FIG. 3. The distance between the center of the eye and the corneal reflection may be computed, where the difference in computed distance between the two eyes may be converted to an objective measure using a HR in the range of previously reported values and an internal calibration factor, as described herein.

Under manual inspection, the Hirschberg test is known to have high variability in the outcome and is meant for obtaining a gross estimate of the deviation. However, a precise measurement can be achieved by employing high-resolution mobile device cameras and specialized image processing algorithms. Since the internal calibration factor, which is the average value of human horizontal visible iris diameter (HVID), is relatively constant throughout human populations, it serves as a relatively robust automatic calibration factor for the mobile device camera. Consequently, the mobile device can be utilized in the manner described herein without having to explicitly measure the HVID for each subject and without major constraints on the positioning of the mobile device camera from the eyes to be imaged. Data presented below demonstrate that use of the population average value of HVID instead of individual values does not substantially affect the accuracy of eye deviation computation. Eye deviation can be measured monocularly with respect to a ground truth, or binocularly (e.g., see FIG. 2) between the two eyes with the subject fixating on a suitable target.

B. Video-Based Cover Test Mode

The mobile device application is capable of measuring eye deviations under dissociated conditions. In certain situations, such as in the case of intermittent strabismus or phoria, the eye deviation is not present when fixating binocularly. The eye deviation can be seen only when binocular fusion is broken (e.g., dissociated condition). In a clinic, such deviations can be measured using a cover test with prism neutralization (CTPN), where an occluder is placed in front of an eye to perform either cover-uncover or alternate-cover tests with prisms. This functionality is adopted in the mobile device application described herein for measurement of latent eye deviations using an automated cover test without using prisms.

Figure 10A:
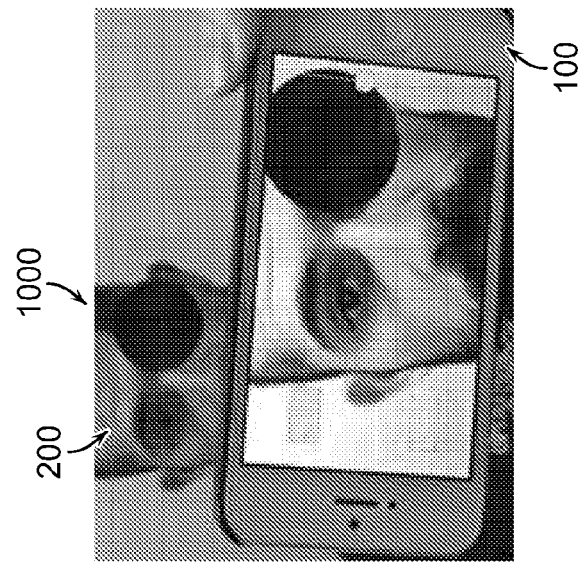
FIGS. 10A-10C are views of an exemplary video-based cover test mode.
Figure 10B:
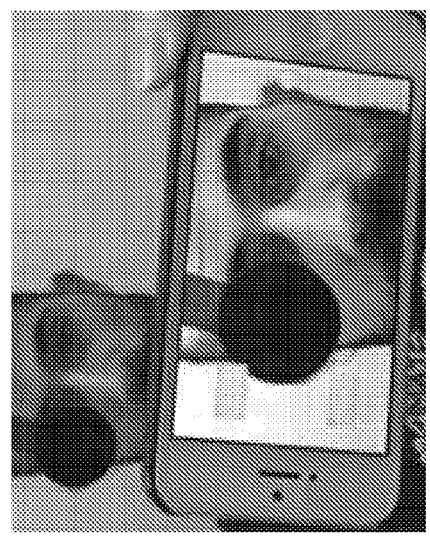
Figure 10C:

To perform a "video-based cover test," the examiner can place the mobile device approximately 10 to 50 cm, or more preferably approximately 20 to 40 cm, or even more preferably approximately 30 cm from the patient's eye and press a button to record a video (one or more serial photos can be captured in other modes, as described above), while the patient fixates on a target binocularly. The patient's binocular fusion is broken by performing a cover sequence of the patient's eyes using an occluder 1000. e.g., cover-uncover (of one eye) or alternate cover (involving both eyes), as demonstrated in FIGS. 10A-10C. As shown in FIGS. 10A and 10B, the eyes of the patient are alternately covered using the occluder 1000, and as shown in FIG. 10C, the eyes of the patient (including the non-dominant eye) are ultimately uncovered. The mobile device 100 can record the entire cover sequence event as a video.

Figure 11:
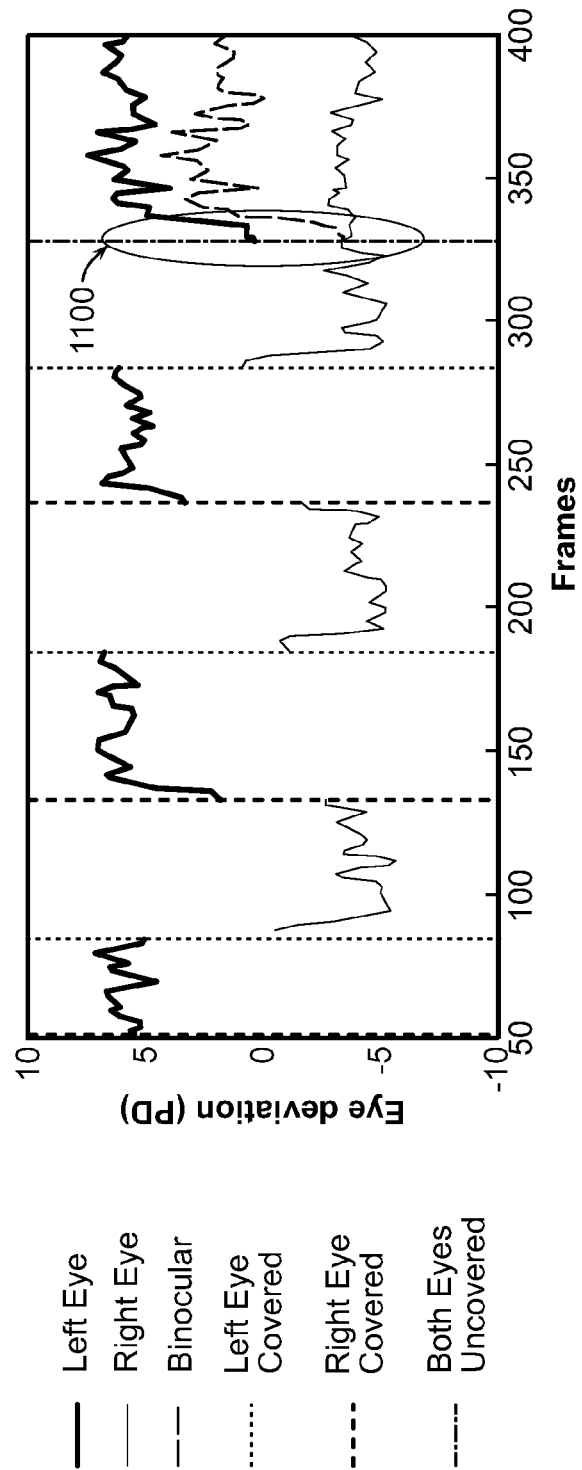
FIG. 11 is a graph showing exemplary eye movement trace obtained when performing the video-based cover test shown in FIGS. 10A-10C.

The video frame just after uncovering the non-dominant eye can be selected for processing the eye deviation. Due to the high frame-rate of video capture (e.g., 30 frames per second), the deviation can be measured just as the eye is uncovered and before it can recover and gain fixation. FIG. 11 shows an example of the eye movement trace obtained when performing the video-based cover test shown in FIGS. 10A-10C, with the mobile device 100 recording the video of this event (i.e., "cover sequence"). The movements of eyes can be seen as they are alternatingly uncovered, and for a brief duration after removing the cover (e.g., occluder 1000), the eye deviation (A) can be measured before the eye moves back into its fixating position. There is a brief duration after removing the cover during which the deviation can be measured (denoted by the shaded zone 1100). To aid in ease of use and consistency of the video cover test performance, the mobile device application can provide audio tones to guide the patient in covering/uncovering the eyes during the cover sequence.

C. Evaluation of Mobile Device Application

Figure 12:
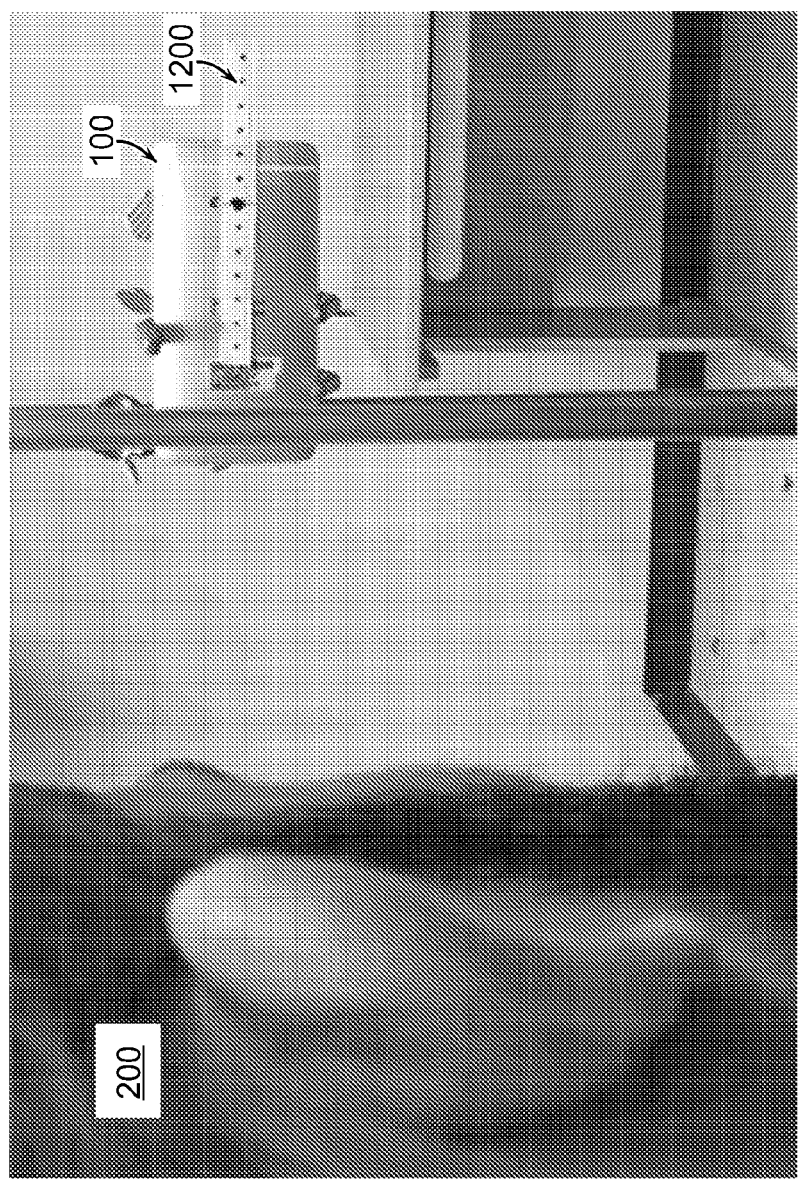
FIG. 12 is a view showing an exemplary evaluation environment of the mobile device application.

The accuracy and reliability of the mobile device application described herein in measuring the absolute angle of deviation was evaluated in a carefully calibrated laboratory setup. As shown in FIG. 12, subjects 200 rested their heads in a chin-rest and faced the rear side of a mobile device 100 that was placed at approximately 30 cm from their eyes. The height of the apparatus was adjusted as needed. The distance of the mobile device's built-in camera 142 to the eyes of the subject 200 was measured manually using a ruler. Fixation targets (black markings 1200 on white background) were pasted on the back surface of the mobile device 100, as shown in FIG. 12, such that they aligned with the camera 142. The reason for such a placement was to ensure symmetric eccentricities of the fixation targets with respect to an obvious reference point. There were 13 targets 1200, placed 1 cm apart and covering an angular range of 26° (about 46Δ) overall to measure eye deviations along the horizontal direction. The subjects were asked to fixate on the targets 1200 only using their right eye while the left eye was patched. This was done to enhance the fixation stability and reduce any possible causes of error due to any other latent binocular vision limitations of the subjects. Measurements were taken for each fixation position in two separate trials so as to determine the test-retest accuracy of the mobile device application.

The application captured an image with a flash at each fixation point 1200. After the application processed the captured image for a given fixation point 1200 (within a fraction of seconds), the examiner instructed the subject to move the gaze to the next point 1200. In case the application failed to record (e.g., due to the subject blinking), measurement was repeated for the current fixation target 1200. The next trial was conducted in the same session after a short break of five minutes.

25 normally sighted subjects without any known strabismus participated in the eye deviation measurement experiment. The subjects were relatively young (between the ages of 20 and 40), and their corrected visual acuity was no worse than 20/30. This group also included those who habitually wore prescription eye glasses; however, they did not wear them during the experiment to avoid issues due to specular reflections interfering with the operation of the application. Only those subjects who could resolve the fixation targets 1 cm apart at 30 cm without wearing their glasses were included in the study.

In a second experiment, phoria measurement was performed using the video-based alternate cover test mode described above in 14 normally sighted non-strabismic young adults (age less than 40). Similar to the earlier setup, the subject 200 rested his or her head in a chin rest and the phone was placed at about 40 cm from the eyes. An accommodative target served as a fixation point which was attached near the mobile device's camera 142. The eyes were alternatingly covered and uncovered by the examiner with an occluder 1000 while the subject maintained fixation. A short video of about two seconds was captured during the cover sequence. Auditory tones generated by the mobile device 100 guided the examiner to change the cover from one eye to another and finally completely remove the cover. The audible tones were timed such that it recorded the last two seconds of cover sequence that included uncovering of both the eyes. Three frames just after uncovering the eyes were selected for processing, and the maximum magnitude of deviation computed in these three frames was recorded as the output of the application. Since the video capture was at high-speed, sometimes the frame just after removal of the occluder 1000 was blurry. To alleviate the inaccuracies in measurement due to the blur, the strategy of using maximum deviation in three consecutive frames after uncovering was employed. Each subject was tested three times with the mobile device application. For comparison, phoria was measured using Modified Thorington (MT) near card (i.e., at 40 cm) twice, and repeated once more if the difference between the first two measurement exceeded 2Δ.

D. Statistical Analysis

Figures 13A, 13B, 13C:
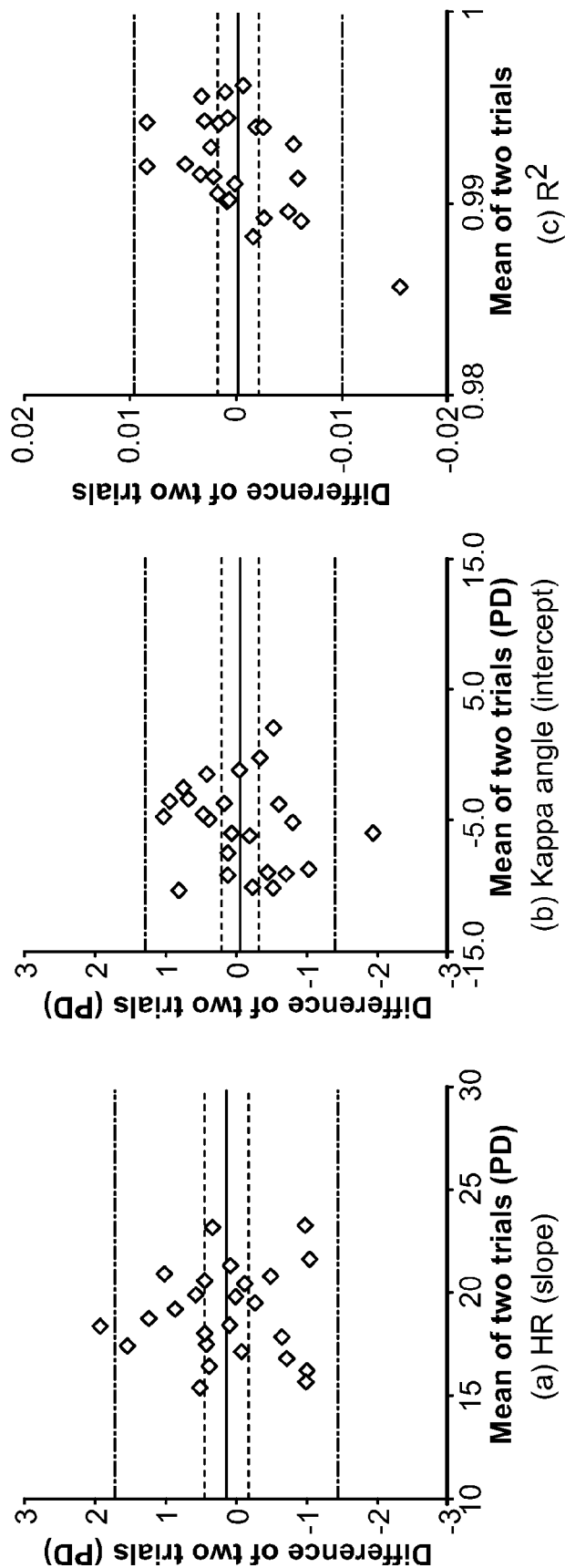
FIGS. 13A-13C are graphs showing exemplary data indicating within-subject test-retest reliability of the deviation measurements by the mobile device application.

The eye deviation measurement results of the mobile device application described herein were manually examined for each fixation point 1200 and any erroneous detections were discarded (e.g., incorrect corneal reflection localization or incorrect limbus boundary estimation). The application computed eye deviation in mm (the pixel level decentration was scaled by the average iris diameter). The amount of angular deviation an eye would undergo for each mm of corneal reflection de-centration is determined by the HR, which varies from person to person. The slope of the line fitting the scatter of the ground truth angular deviations versus the mm deviations of the eye measured by the app gives the estimated HR for an individual, while the intercept is indicative of the kappa angle (i.e., the angle between the visual axis and the optical axis). The test-retest reliability of the application in estimating the HR and kappa angle for each subject was also measured. A Bland-Altman or Tukey mean difference plot with 95% confidence interval (CI) of the distribution was used to visualize these results, as shown in FIGS. 13A-13C. Furthermore, in order to determine the accuracy of the application in estimating absolute eye deviation angles, the measurements for each individual around the central fixation point were normalized and scaled using the population averaged HR. The average HR used for a subject 200 was calculated from all the remaining subjects (excluding the data from that particular subject). Ground truth measures of the HVID were factored in to reconcile a potential source of between-subject variability.

E. Results

With two trials performed for each subject, and 13 fixation points 1200 per trial, the mobile device application processed 26 images per subject and 650 images in total. Out of these, the application was able to correctly process 629 images.

FIGS. 13A-13C shows the within-subject test-retest reliability of the deviation measurements by the application for the slope (HR), intercept (angle-kappa), and the $R^2$ values for lines fitting the measured and the ground truth eye deviation data. The Bland-Altman plots shown in FIGS. 13A-13C include dash and dot lines representing the 95% CI of agreement between two measurements. The solid line represents the mean difference between two measurements over the entire population and the dashed lines are its 95% CI limits.

In detail, the average±standard estimated HR, kappa angle, and $R^2$ over the study population were 19.26±1.78 Δ; 5.49±3.48Δ (nasal); and 0.992±0.0026, respectively. The average difference in HR, kappa angle, and $R^2$ values estimated in two trials were 0.13±0.31 Δ; −0.0181±0.29; and −0.0004±0.002, respectively. The 95% CI of the agreement between the HRs, kappa angles, and $R^2$ values estimated in two trials were ±1.57 Δ, ±1.44Δ, and ±0.0098, respectively, as demonstrated in FIGS. 13A-13C.

Figure 14:
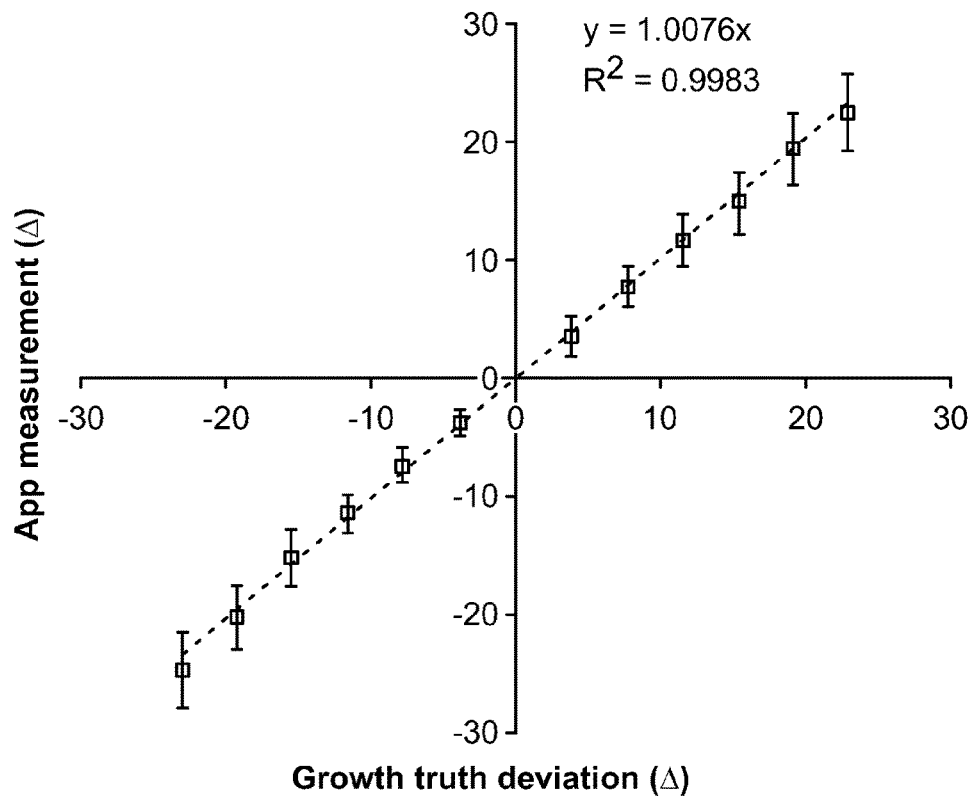
FIG. 14 is a graph showing an exemplary comparison of measured deviation using the mobile device application and the ground truth for different angles of fixation.

Meanwhile, FIG. 14 shows a comparison of measured deviation (normalized) using the mobile device application and the ground truth for different angles of fixation. Each point on the graph represents the mean deviation measured over all subjects, while the error bars represent the standard deviation. The dashed line represents the regression line. The mobile device application measurements were normalized and scaled using the population average HR and HVID in order to scale the measurements to angular deviations. A regression analysis with the ground truth serving as an independent variable and the measured deviation as a dependent variable led to the following results, as shown in FIG. 14: slope=1.0076 ($p<0.001$); intercept=−0.1406 ($p=0.48$); and $R^2$=0.998.

Figure 15:
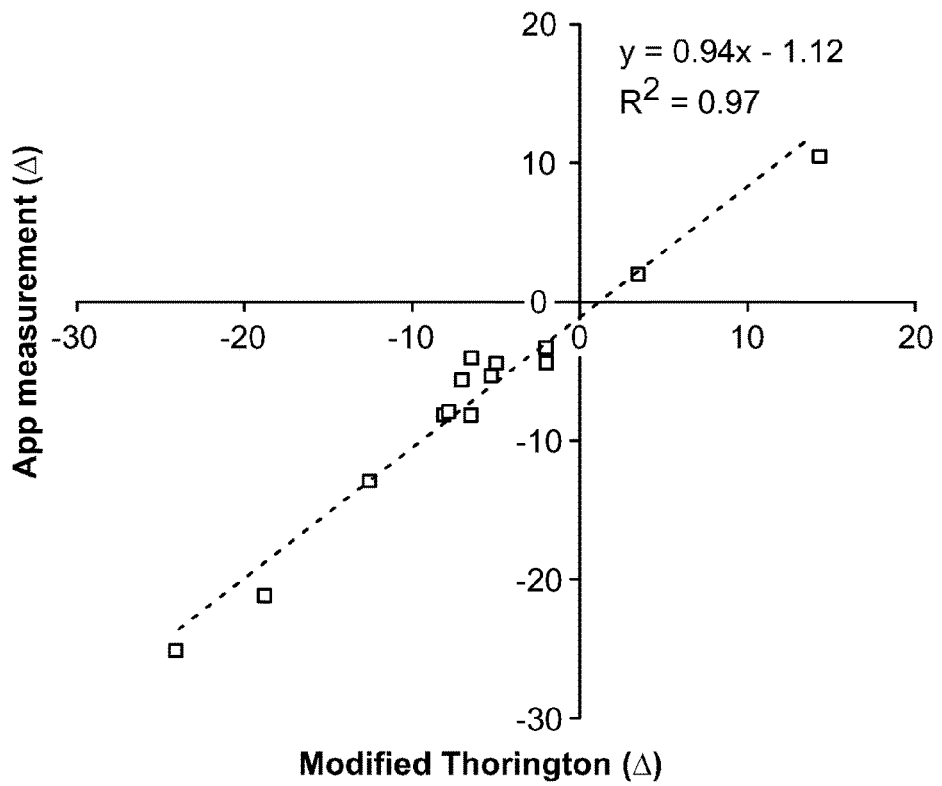
FIG. 15 is a graph showing exemplary results of phoria measurements for subjects using the mobile device application.

FIG. 15 shows the results of phoria measurements for 14 subjects with the mobile device application and using a Modified Thorington (MT) method that is commonly used in clinics. As shown in FIG. 15, phoria measurements of the mobile device application closely follow the clinical measurements (n=14; slope: 0.94; intercept: −1.12; $R^2$=0.97; $p<0.001$). The overall RMSE between the application and MT method was 1.7Δ. There was no correlation between the phoria and the difference in the two measurement methods (r=−0.32; p=0.265). Within the study population, more people had exophoria than esophoria. Within-subject MT measurements were within 1Δ for ten out of 14 subjects and within 2Δ for 13 out of 14 subjects. The subject with largest difference between the application and MT (3.9Δ) also showed highest within-subject difference in MT measurement (5Δ). With the application, there was no significant difference between trials within subjects (repeated measures ANOVA: F(2,41)=0.198; p=0.98). Overall with the application, the mean and 95% CI of the within-subject phoria measurement difference was −0.3Δ and ±2.6Δ, respectively. In other words, the correlation between the difference and the deviation measured with MT was not significant, indicating that there was no systematic error.

F. Discussion

The results described above show that the measurements obtained by the mobile device application described herein are accurate, repeatable, and comparable to clinical measurements in normally sighted non-strabismic adults. Within-subject (or subject-specific) parameters such as the HR and kappa angle estimated by the two independent application measurements are consistent (the 95% CI of difference 1.54). A close linear fit to the underlying eye deviation data to obtain subject-specific parameters, such as the HR and kappa angle, is indicated by high $R^2$ values (≈0.99). Thus, the mobile device application described herein can provide meaningful clinical information, as the results indicate a strong correlation between such measurements and traditional clinical methods, (e.g., MT).

With phoria measurements, the results show that the mobile device application provides meaningful clinical information. The results indicate a strong correlation between the application measurements and the MT method. Furthermore, measuring phoria requires dissociation between the two eyes, and the video-based cover test mode of the application was ideal for conducting such measurements. The results also suggest that the same procedure can be employed for measuring intermittent strabismus.

The use of HVID allows for use of the iris center instead of pupil center as the reference for computing the corneal reflection decentration. The iris center can be a more robust reference for measuring ocular alignment, especially when computing binocular differences. Another advantage of using iris center is that the limbus boundary is better delineated than the pupil boundary in visual spectrum, especially in case of people with dark irises. Notably, so long as the patient's eyes are symmetric, an off-center pupil will not affect the strabismus results computed with the application.

Accordingly, techniques are described herein that allow for complex ocular misalignment assessments using widely accessible mobile devices, such as a smart phone, tablet, and the like. The mobile device can leverage the native hardware already installed in many modern mobile devices, such as a camera and a flash. Once a photograph of eyes of a patient is captured, the processor analyzes the photograph to detect various features in the patient's eyes and can then measure a magnitude of ocular misalignment. The entire processing is performed on the mobile device itself, rather than sending the captured photographs to a remote server for processing.

Advantageously, the mobile application facilitates a quick, convenient, and inexpensive way to measure ocular misalignment, particularly in the case of uncooperative patients such as non-verbal children or adults with severe brain injuries. The ability to provide objective measurements quickly and conveniently can be highly beneficial to clinicians who see large volumes of patients on a regular basis. Alternatively, the application can be used at home, for example, by parents who suspect their kids might have strabismus. Greater accessibility to ocular screenings can help alleviate missed diagnoses in a case where a condition manifests intermittently. The application is also well suited for telemedicine, which can be useful in remote, underserved areas, or for remote follow-up of treatment without the patient having to visit the doctor. Further, due to the high-resolution capabilities of modern mobile device cameras, the application can measure small angle strabismus (e.g., less than 5 prism diopters (PD)) that is otherwise difficult to detect using conventional clinical methods. Also, the application is robust in that it handles a variety of imaging conditions and variability of eye appearance between subjects.

While there have been shown and described illustrative embodiments that provide for a mobile device application for ocular misalignment measurement, it is to be understood that various other adaptations and modifications may be made within the spirit and scope of the embodiments herein.

For instance, while a mobile device is frequently mentioned throughout the present disclosure, the techniques described herein may also be implemented on desktop computers or similar machines. Thus, the embodiments of the present disclosure may be modified in any suitable manner in accordance with the scope of the present claims.

The foregoing description has been directed to embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A mobile device comprising:
   an image acquisition unit configured to acquire an image of first and second eyes of a patient;
   a light source configured to provide light to reflect from an optical surface of the first and second eyes of the patient;
   a processor configured to:
      obtain ocular misalignment measurements including at least one of a magnitude and a direction of ocular misalignment in the first and second eyes of the patient;
      detect at least one of an iris and a pupil in the first and second eyes of the patient;
      calculate at least one of an inter-pupillary distance and an iris diameter of the patient; and
      calculate a Hirschberg ratio of the patient based on the ocular misalignment measurements and at least one of the inter-pupillary distance or the iris diameter of the patient.

2. The device of claim 1, wherein the processor is further configured to detect a reflection on a corneal surface of the first eye of the patient and a reflection on a corneal surface of the second eye of the patient using the acquired image, and configured to compare a position of the reflection in the first eye to a position of the reflection in the second eye.

3. The device of claim 2, wherein the processor is further configured to:
   detect a reference point in the first eye and a reference point in the second eye using the acquired image;
   calculate a first distance between a position of the reference point in the first eye and the position of the reflection in the first eye;
   calculate a second distance between a position of the reference point in the second eye and the position of the reflection in the second eye;
   calculate a difference between the first distance and the second distance; and
   diagnose a condition of the patient based on the calculated difference between the first distance and the second distance,
   wherein the reference points in the first and second eyes are a center of an iris or pupil of the patient.

4. The device of claim 3, wherein the processor is further configured to measure the positions of the reflections in the first and second eyes and the positions of the reference points in the first and second eyes in image space using the acquired image.

5. The device of claim 4, wherein the processor is further configured to convert the first distance and the second distance into degrees or prism diopters using the Hirschberg ratio and an internal calibration factor based on iris diameter.

6. The device of claim 3, wherein the processor is further configured to:
   compare the calculated difference between the first distance and the second distance to a predetermined misalignment threshold;
   diagnose the condition of the patient based on the comparison of the calculated difference to the predetermined misalignment threshold; and
   determine that an ocular misalignment condition is present in the patient when the calculated difference is greater than or equal to the predetermined misalignment threshold.

7. The device of claim 1, wherein the processor is further configured to diagnose a condition of the patient or a risk factor of the patient developing a condition associated with ocular misalignment based on the ocular misalignment measurements.

8. The device of claim 1, wherein the processor is further configured to detect an iridoscleral border and a pupillary margin of the eyes of the patient using the acquired image using an adaptive threshold algorithm.

9. A hand held device comprising:
   an image acquisition unit configured to acquire an image of first and second eyes of a patient;
   a light source configured to provide light to reflect from an optical surface of the first and second eyes of the patient;
   a processor configured to:
      determine ocular misalignment measurements of the first and second eyes, the ocular misalignment measurements including at least a magnitude and a direction of ocular misalignment in the first and second eyes of the patient;
      measure a Kappa angle between an optical axis and a visual axis of the first and second eyes of the patient based on the acquired image;
      diagnose a condition of the patient based on the measured Kappa angle;
      determine a deviation of the first and second eyes from the Kappa angle; and;
      determine which eye of the first and second eyes of the patient is misaligned and measure a fixation reliability index of the non-misaligned eye based on the deviation of the non-misaligned eye from the Kappa angle.

10. The device of claim 9, wherein the processor is further configured to diagnose a misalignment direction of the misaligned eye based on the Kappa angle.

11. The device of claim 9, wherein the processor is further configured to calculate at least one of an inter-pupillary distance and an iris diameter of the patient; and perform at least one calculation based on at least one of the ocular misalignment measurements, the inter-pupillary distance, and the iris diameter of the patient.

12. The device of claim 9, wherein the processor is further configured to detect at least one of an iris and a pupil in the first and second eyes of the patient.

13. The device of claim 9, wherein the processor is further configured to calculate a Hirschberg ratio of the patient.

14. The device of claim 9, wherein the image acquisition unit is configured to acquire a plurality of images of the first and second eyes of the patient; and
   wherein the processor is configured to determine an image quality of the acquired plurality of images, and configured to use an image having a highest image quality among the acquired plurality of images when determining the ocular misalignment measurements.

15. The device of claim 9, wherein the image acquisition unit is configured to acquire a plurality of images of the first and second eyes of the patient; and wherein the processor is configured to obtain the ocular misalignment measurements in each of the acquired images of the plurality of images, generate a composite of the obtained ocular misalignment measurements, and determine an overall ocular measurement based on the generated composite.

16. The device of claim 9, further comprising one or more motion sensors, wherein the processor is further configured to compensate for rotation of the device during image acquisition using measurements obtained by the motion sensors.

\* \* \* \* \*

UNITED STATES PATENT AND TRADEMARK OFFICE
CERTIFICATE OF CORRECTION

PATENT NO. : 11,786,117 B2
APPLICATION NO. : 17/084412
DATED : October 17, 2023
INVENTOR(S) : Matteo Tomasi et al.

It is certified that error appears in the above-identified patent and that said Letters Patent is hereby corrected as shown below:

In the Specification

Column 12, Line 56, "call" should be --can--.

Column 19, Line 41, "464" should be --46$\Delta$--.

Column 19, Line 42, "symbol A)" should be --symbol $\Delta$)--.

Column 21, Line 16, "(A)" should be --($\Delta$)--.

Column 24, Line 3, "difference 1.54)" should be --difference $\approx$1.5$\Delta$)--.

Signed and Sealed this
Thirteenth Day of February, 2024

Katherine Kelly Vidal
Director of the United States Patent and Trademark Office